(12) United States Patent
Minamigawa et al.

(10) Patent No.: US 7,247,481 B2
(45) Date of Patent: Jul. 24, 2007

(54) PROCESS FOR CULTURING CELLS SAMPLED FOR BIOPSY

(75) Inventors: Kazuhiko Minamigawa, Kashiwara (JP); Hisayuki Kobayashi, Osaka (JP); Toshikazu Takano, Yao (JP)

(73) Assignee: Nitta Gelatin Inc., Osaka (JP)

( * ) Notice: Subject to any disclaimer, the term of this patent is extended or adjusted under 35 U.S.C. 154(b) by 428 days.

(21) Appl. No.: 10/122,220

(22) Filed: Apr. 16, 2002

(65) Prior Publication Data
US 2003/0194805 A1 Oct. 16, 2003

(51) Int. Cl.
*C12N 5/06* (2006.01)
*C12N 5/08* (2006.01)
*C12N 11/02* (2006.01)

(52) U.S. Cl. .................. 435/395; 435/177; 435/325; 435/366; 435/384

(58) Field of Classification Search ............. 435/177, 435/180, 325, 395
See application file for complete search history.

(56) References Cited

U.S. PATENT DOCUMENTS

| | | | | |
|---|---|---|---|---|
| 4,743,552 A | | 5/1988 | Friedman et al. ...... 435/240.23 |
| 5,143,835 A | * | 9/1992 | Nakatsugawa et al. ..... 435/167 |
| 5,356,793 A | | 10/1994 | Koezuka et al. .............. 435/32 |
| 5,543,327 A | | 8/1996 | Yen-Maguire et al. ... 435/287.9 |
| 5,712,161 A | | 1/1998 | Koezuka et al. ............. 435/382 |
| 5,741,782 A | | 4/1998 | Brockbank et al. |
| 6,008,007 A | | 12/1999 | Fruehauf et al. .............. 435/29 |

FOREIGN PATENT DOCUMENTS

| | | |
|---|---|---|
| EP | 1 018 547 A | 7/1999 |
| GB | 901673 | 7/1962 |
| JP | A-316479/1992 | 11/1992 |
| JP | A-327470/1994 | 11/1994 |
| JP | 728757 | 4/1995 |
| JP | 2565843 | 10/1996 |
| JP | 10115612 | 5/1998 |
| JP | 2879978 | 1/1999 |
| JP | A-507953/2000 | 6/2000 |
| JP | A-253871/2000 | 9/2000 |
| WO | WO 95/18216 | 7/1995 |
| WO | WO 97/36479 A1 | 10/1997 |

OTHER PUBLICATIONS

Furukawa et al., "Increased Drug Resistance of Cultured Human Cancer Cell Lines in Three-Dimensional Cellular Growth Assay Using Collagen Gel Matrix", Journal of Surgical Oncology, New York, NY, vol. 49, No. 2, Feb. 1, 1992, pp. 86-92.

Forrer et al., "Comparison of Vancomycin and Penicillin for Viral Isolation", Journal of Clinical Microbiology, US, vol. 16, No. 2, Aug. 1982, pp. 295-298.

\* cited by examiner

*Primary Examiner*—David M. Naff
(74) *Attorney, Agent, or Firm*—Roylance, Abrams, Berdo & Goodman, L.L.P.

(57) ABSTRACT

The present invention provide: a novel process for culturing animal cells and a kit for culturing animal cells, in which, even if the number of cells as sampled for biopsy is extremely small, the proliferation can sufficiently be maintained so as to enable to carry out various culture and/or tests, especially anticancer agent sensitivity tests, and the contamination with bacteria can be inhibited without damaging physiological activity of cells, especially sensitivity to anticancer agents. The process for culturing animal cells, according to the present invention, comprises the step of culturing a sample containing animal cells obtained from living body tissue in order to subject the sample to further culture and/or a test, with the process being characterized in that a culture medium is used wherein the culture medium has a proliferating action and physiological activity-retaining action on the animal cells, and further has a killing action and/or multiplication-inhibition action on bacteria.

7 Claims, 12 Drawing Sheets

Concentration of vancomycin as added (mg/ml)

Concentration of vancomycin as added (mg/ml)

Concentration of vancomycin as added (mg/ml)

Concentration of vancomycin as added (mg/ml)

Surface area of 5.5 cm²

PROCESS FOR CULTURING CELLS SAMPLED FOR BIOPSY

BACKGROUND OF THE INVENTION

A. Technical Field

The present invention relates to a process for culturing animal cells obtained from living body tissue. More particularly, the invention relates to a process for culturing animal cells obtained from living body tissue in order to use them for further culture and/or a test.

B. Background Art

Anticancer agent sensitivity tests sometimes have been carried out using subcultured cancer cells hitherto, but for the purpose of evaluating effects of anticancer agents upon respective individuals, methods of evaluating the effects of the anticancer agents by utilizing so-called primary culture, in which samples taken from a living body are directly cultured, are widely employed. However, when cancer cells were taken from living body tissue as a sample and then used, there were problems such that: a necessary and sufficient amount of live cells maintaining proliferativity cannot be obtained, and in addition, the sample contains normal cells other than the aimed cancer cells, and further contains many other components such as bacteria.

Accordingly, as a method for efficiently carrying out anticancer agent sensitivity tests, for example, the following method has been applied in recent year: a method in which primary cells containing cancer cells in a collagen gel is embedded, and then cultured. Even if the absolute amount of the cancer cells as used for the tests is small, the cancer cells can favorably be proliferated in the collagen gel. In addition, even if the collagen gel is contaminated with cells other than the cancer cells such as fibroblast cells and each is grown and extended, they can easily be distinguished morphologically. Therefore, the evaluation of the sensitivity of only the cancer cells both the anticancer agents are added thereto and not can easily be carried out.

Furthermore, for the purpose of enhancing the accuracy of the tests, well known is a method that involves: placing a droplet of a cancer-cell-containing collagen solution on a surface of a supporting base material; allowing the droplet to gel; and forming and embedding a globular collagen gel, in order to culture the cancer cells under more favorable density and circumstances to proliferated the cancer cells more easily (Japanese Patent No. 2879978).

These methods may be theoretically and technically preferred, but, when such as anticancer agent sensitivity tests are carried out using cells sampled for biopsy as actually sampled from living bodies, the test success rate is still low, and the level of the tests is not sufficient to say that it is in on a realistic and practical level in the clinical. As to its cause, the following is mentioned first: there are many cases where cells of which the number has a level such that the test can sufficiently be carried out cannot be collected, or the cells cannot be collected at all. In order to solve this, it is thought necessary to reduce the loss of the number of the cells as sampled from the living bodies as low as possible. However, the washing step regarded as necessary in conventional methods has problems such that: it is very difficult to carry out the step for a very slight sample amount of biopsy materials; the sufficient washing is impossible; and further the yield is very low and the loss is increased. As to the second cause, the following is mentioned: the culture cannot be continued often because of the contamination with such as bacteria. It is natural to cause the possibility of the contamination on the operation, and tissue sampled in vivo especially from such as intestines includes *Escherichia coli* and various bacteria that are bacteria ordinary living in vivo. Therefore, under the present circumstances, even if the process of the above-mentioned washing step is gone through, the inhibition of the contamination still cannot entirely be performed, resulting in serious problems.

SUMMARY OF THE INVENTION

A. Object of the Invention

Accordingly, an object of the present invention is to provide: a novel process for culturing animal cells; and a kit for culturing animal cells; by which: even if the number of cells as sampled for biopsy is extremely small, the proliferation can be maintained sufficiently to enable the implementation of such as various culture and/or tests, especially anticancer agent sensitivity tests, and the contamination with bacteria can be inhibited without damaging physiological activity, especially, sensitivity to anticancer agents, of cells.

B. Disclosure of the Invention

The present inventors diligently studied to solve the above-mentioned problems. As a result, when they culture and proliferate cells sampled for biopsy in order to use them for further culture and/or a test, they took note of a culture medium as used during the culture, and then they found that: if a culture medium having specific action and effect is used as this culture medium, all the above-mentioned problems can once be solved.

That is to say, a process for culturing animal cells under embedded conditions, according to the present invention, comprises the step of culturing sample cells containing animal cells obtained from living body tissue in order to subject the sample cells to further culture and/or a test, with the process being characterized in that a culture medium is used wherein the culture medium has a proliferating action and physiological activity-retaining action on the animal cells, and further has a killing action and/or multiplication inhibition action on bacteria.

In addition, a kit for culturing animal cells, according to the present invention, is a kit that comprises the following constituent articles: a collagen solution; a concentrated culture medium; a reconstituting buffer solution; an enzyme for dispersing cells; a tube for a culture supporting base; a culture medium for preliminary culture; a serum-free culture medium; and a cell-dyeing agent.

These and other objects and the advantages of the present invention will be more fully apparent from the following detailed disclosure.

DETAILED DESCRIPTION OF THE INVENTION

Figure 1:
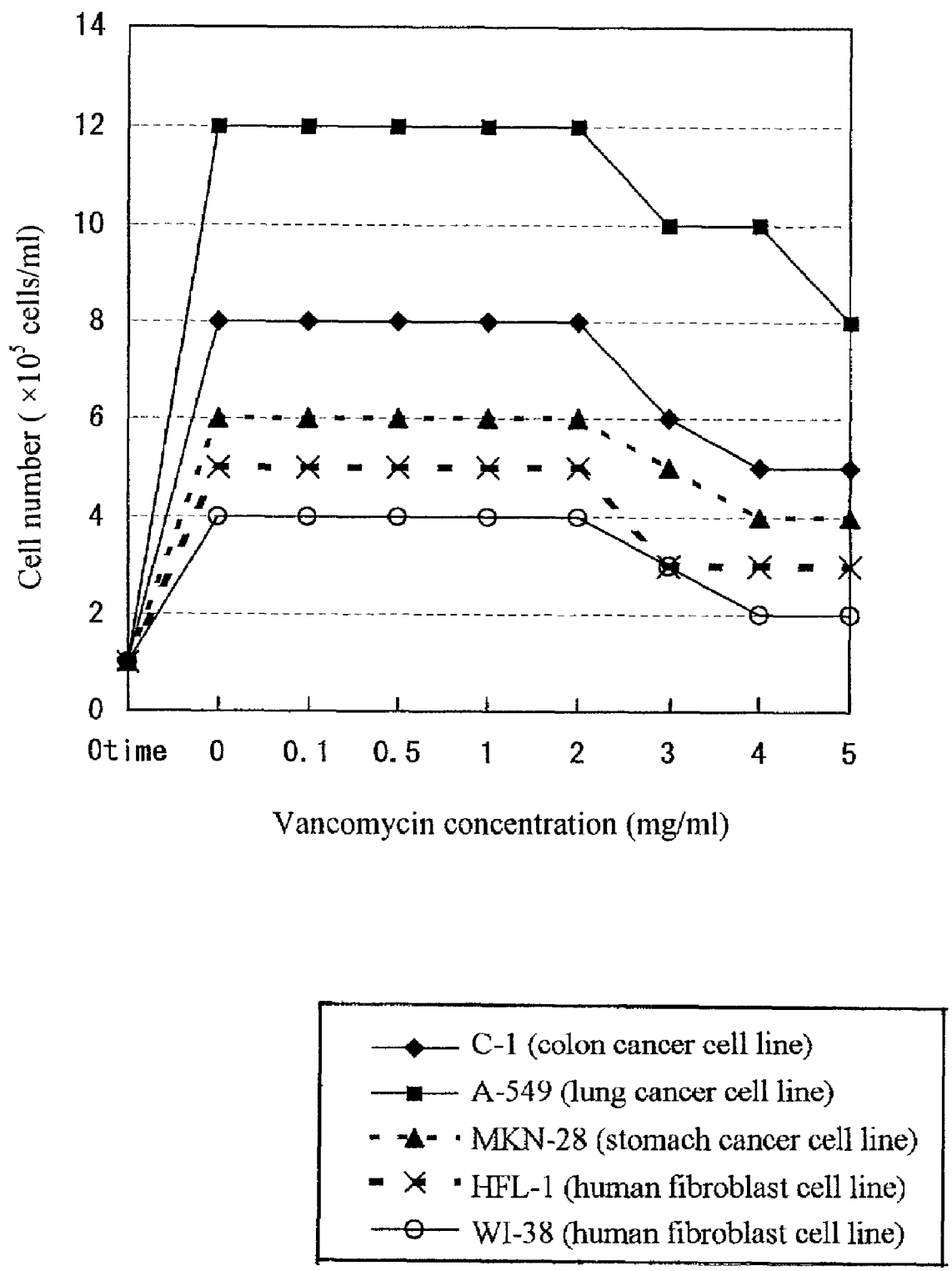
FIG. 1 is a graph representing an influence of the vancomycin concentration in the preliminary culture step upon the cell proliferativity in the preliminary culture step (concerning a cancer cell line and a fibroblast cell line).

The process for culturing animal cells, according to the present invention, comprises the step of culturing sample cells containing animal cells obtained from living body tissue in order to subject the sample cells to further culture and/or a test, with the process be in characterized in that a culture medium is used wherein the culture medium has a proliferating action and physiological activity-retaining action on the animal cells, and further has a killing action and/or multiplication-inhibition action on bacteria.

Herein, in the present invention, it is favorable that the sample containing animal cells obtained from living body tissue is usually a section of internal organs or tissue (living body tissue) separated from a living body. Such an animal cell obtained from living body tissue, that is, a cell as sampled for biopsy, is called a primary cell and used for what is called primary culture. In addition, typical examples of the primary cell include a tumor cell. Of this tumor cell, a malignant tumor cell, that is, a cancer cell is an object particularly when the anticancer agent sensitivity tests are carried out. The sample containing animal cells obtained from living body tissue, that is, a culture sample, most preferably consists of cells which are objects of culture (e.g. cancer cells) alone, but usually it also contains normal cells such as fibroblast cells as a portion of living body tissue. In addition, it often occurs that dead cells, in addition to live cells, are contained as the aimed cells themselves.

In addition, subjecting the sample to further culture and/or a test in the present invention may mean using at least one portion or the entirety of a sample cultured by the present invention culturing process as a sample for desired culture to be carried out newly and continuously, or using it as a sample which is a direct object of test when desired tests (for examples, the anticancer agent sensitivity tests as mentioned above, co-culturing tests, and various genetic diagnoses) are carried out, or also using it as a sample to be subjected to a series of steps comprising the above desired culture and desired test. Among them, particularly the present invention culturing process can favorably be applied to a step that is a preceding stage of anticancer agent sensitivity tests. The present invention culturing process can favorably be applied also to all other objects and steps to such an extent that they can be carried out sufficiently.

Next, the culture medium as mentioned in the present invention has a proliferating action and physiological activity-retaining action on the animal cells, and further has a killing action and/or multiplication-inhibition action on bacteria.

The aforementioned proliferating action may be at least an action of maintaining the cell number of such as the aimed animal cells (cells sampled for biopsy) or animal cell lines without reducing it, favorably an action of increasing the cell number.

The aforementioned physiological activity-retaining action may be at least an action of giving some physiological activity to such as the aimed animal cells (cells sampled for biopsy) or animal cell lines still even after the culture, favorably an action of retaining or improving the same physiological activity as is when sampled from living body tissue still after the culture. In specific examples thereof, animal cells (cells sampled for biopsy) or animal cell lines, resultant from culture, have reactivity to such as agents when the cells are used for such as tests for sensitive to agents.

The killing action and/or multiplication-inhibition action on bacteria is favorably an action effect which prevents the culture using the present invention culturing process or another culture as carried out after this culture, from becoming uncontinuable because of the contamination with bacteria. At the same time, a conventional washing step of washing cells after the cells are sampled from a living body (a step of removing bacteria and various germs) can be simplified by this action effect. Therefore, the loss of the cell number can be decreased when the washing is carried out. Accordingly, as a result, even if the cell number of cells as sampled is extremely small, there is no loss of the cell number, and the activity can be maintained or proliferated, to such an extent that the cells can be used for sensitivity tests, in a state of no unfavorable influence because of the contamination. In specific examples thereof, the success rate in the case of carrying out tests such as anticancer agent sensitivity tests can be raised to higher than before. Incidentally, the bacteria as mentioned herein mainly includes bacteria ordinarily living in vivo (for example, *Escherichia coli*), which have mingled when cells are sampled from living body tissue, especially from tissue such as digestive apparatus, and also includes such as bacteria which have mingled from such as air when the culturing procedure is carried out. In addition, in order to make the culture medium have this action effect, 1) such as some agent may be added to the culture medium, 2) the composition of the culture medium of the culture medium itself may be adjusted so that such as multiplication of the aimed bacteria will be inhibited, thereby obtaining the same effect; and 3) the temperature and pH are adjusted so that the multiplication of aerobic bacteria can be inhibited. There is especially no limitation. However, among these, it is favorable to make the culture medium have the aforementioned action effect by adding antibiotic agents including antibiotics as the agents.

The aforementioned antibiotic agents are not especially limited, but specific examples thereof include at least two members selected from the group of antibiotics consisting of cell-wall-synthesis inhibitors, protein-synthesis inhibitors, nucleic-acid-synthesis inhibitors, and antifungal agents. Among these, it is favorable to include at least one member selected from the group consisting of the cell-wall-synthesis inhibitors. Examples of the cell-wall-synthesis inhibitors favorably include: β-lactam series, such as penicillin series, cephem series, monobactam series, and carbapenem series, phosphomycin; vancomycin; and Teicoplanin. Examples of the protein-synthesis inhibitors include: aminoglycoside series; macroride series; lincomycin series; tetracycline series; and chloramphenicol series. Examples of the nucleic-acid-synthesis inhibitors include: ST synthetic compounds, and synthesized antimicrobial agents, such as pyridocarboxylic acid series, quinolone series, and rifampicin. Examples of the antifungal agents favorably include polyene series.

As to the antibiotic agent, only the two antibiotics may be selected and used, or at least three thereof may jointly be used. When at least three are selected and jointly used, there is no especial limitation with regard to examples of favorable combinations thereof. Specific examples include a combination of four kinds comprising penicillin, kanamycin, fungizone and vancomycin. As to the concentration of each antibiotic as used, the concentration of penicillin is favorably in the range of 125 µg/ml to 2 mg/ml, more favorably 250 µg/ml to 2 mg/ml, still more favorably 500 µg/ml to 2 mg/ml, particularly favorably 1 to 2 mg/ml. The concentration of the kanamycin is favorably in the range of 64 µg/ml to 2 mg/ml, more favorably 125 µg/ml to 2 mg/ml, still more favorably 250 µg/ml to 2 mg/ml, particularly favorably 0.5 to 2 mg/ml. The concentration of the fungizone is favorably in the range of 0.32 to 5 µg/ml, more favorably 0.64 to 5 µg/ml, still more favorably 1.25 to 5 µg/ml, particularly favorably 2 to 5 µg/ml, most favorably 2.5 to 5 µg/ml. The concentration of vancomycin is favorably in the range of 0.01 to 3 mg/ml, more favorably 0.1 to 2 mg/ml, still more favorably 0.25 to 2 mg/ml, particularly favorably 0.5 to 2 mg/ml, more particularly favorably 1 to 2 mg/ml, most favorably 2.0 mg/ml. When the culture medium in the present invention culturing process includes an antibiotic agent having the kind (or its combination) in the range of the concentration as used in the above way, the culture medium does not have unfavorable influences such as toxicity to animal cells, and can display sufficient action effects (killing action and/or multiplication-inhibition action) on bacteria as targets.

For the same reason, Examples of favorable other combinations using at least three kinds of the above antibiotic agents are not especially limited. Specific examples thereof favorably include: 1) penicillin, gentamycin, (or minomycin), vancomycin, and fungizone; 2) cephamycin (or cephalosporin), kanamycin (gentamycin or minomycin), vancomycin, and fungizone; 3) penicillin, kanamycin, (or gentamycin, minomycin, cephamycin, or cephalosporin), phosphomycin, vancomycin, and fungizone; 4) penicillin, kanamycin (or gentamycin, minomycin, cephamycin, or cephalosporin), ST synthetic compounds (or other nucleic-acid-synthesizing agents), vancomycin, and fungizone. As to the concentration of the gentamycin, minomycin, cephamycin, and cephalosporin as used in the above other favorable combination example, the concentrations of the gentamycin, minomycin, cephamycin, and cephalosporin are favorably in the ranges of: 0.5 to 1.0 mg/ml, 0.1 to 0.2 mg/ml, 1 to 2 mg/ml, and 1 to 2 mg/ml respectively.

Favorable examples of the usable culture medium in the present invention culturing process include serum culture mediums containing serum, and serum-free culture mediums being free from serum, and either can be used in the present invention. Favorable examples of the serum include FBS (fetal bovine serum), FCS (fetal calf serum), HS (horse serum), or unworkable FBS, and the FBS is more favorable.

The serum-free culture mediums are characterized by containing no serum, and on the other hand conventional culture mediums used for cell culture contain serum as a component. The serum-free culture medium is prepared by combining various chemical substances necessary for culturing, other than serum. Particularly, the serum-free culture medium can suppress the proliferation of fibroblast cells effectively and can inhibit the contraction of collagen gel. In the case where the serum-free culture medium, the specific components and their proportions thereof may be determined as needed, but the composition having good proliferativity of the aimed animal cells (for example, cancer cells) and inhibiting the proliferation of other cells is favorable.

On the other hand, as to the serum culture medium, usually that which has a serum concentration of about 0.001 to about 5.0% is favorably used, but good results are sometimes obtained even by using that of which the serum concentration is in the range of about 5 to about 20%.

In addition, even if the usable culture medium in the present invention culturing process is made to contain dextran sulfate, the contraction of collagen gel can be inhibited. The reason therefor is because the dextran sulfate also has the effect of inhibiting the proliferation of fibroblast cells in the same way as of the serum-free culture medium, and the dextran sulfate can be used instead of preparing the serum-free culture medium. It is favorable that the ratio of the dextran sulfate as added to the culture medium is in the range of 1.5 to 100 µg per 1 ml of the culture medium, and it is more favorable that the ratio of the dextran sulfate having a molecular weight of not less than 50,000 is in the range of 3.0 to 100 μg, and it is still more favorable that the ratio of the dextran sulfate having a molecular weight of not less than 500,000 is in the range of 1.5 to 50 μg. Whichever of the above-mentioned serum culture medium and serum-free culture medium may be used, the dextran sulfate can be added thereto.

The sample (culture sample) as used in the present invention culturing process is a sample containing animal cells sampled from living body tissue. However, these animal cells, that is, primary cells, are favorably primary cells (what are called low invasive sampling cells) obtained by a low invasive sampling method. In addition, these low invasive sampling cells are particularly favorably cells that are excision or test-puncture sampled for the purpose of such as medical diagnosis, curing of diseases, and judgment of prognosis, and is obtained from such as various biopsy cells, materials below thoracoscope or laparoscope, ascites, and malignant pleural fluid.

After the sampling, the sample (culture sample) as used for the culture employing the present invention culturing process is favorably subjected to dispersing treatment, or separating and dispersing treatments beforehand when the occasion demands.

The separating treatment is not especially limited, but it is favorably the treatment such that a culture sample is divided into small pieces in order to enhance the effect of the dispersing treatment that is carried out after the separating treatment. More particularly, this treatment is favorably mechanically separating treatment. Among these, the fine-cutting treatment with such as cesisers, tweezers, and razors is favorable.

The dispersing treatment is not especially limited, but favorable examples thereof include treatment of removing cells other than the aimed animal cells in living body tissue (for example, cancer cells) or intercellular substances, or treatment of removing other substances that can inhibit subsequent various tests. More particularly, these treatments are favorably enzymatic dispersing treatments, and such as collagenase, hyaluronidase, DNase, elastase, and dispase are favorable as the enzyme as used then.

The culture sample as used for the above-mentioned dispersing treatment and/or separating treatment may be a slight amount of 0.001 to 1 g of tissue. When this dispersing treatment and/or separating treatment are carried out, the animal cells (primary cells) are isolated from living body tissue.

Such as treatment conditions of the aforementioned dispersing treatment and/or separating treatment are provided in the following ways 1) to 3), depending upon the size of the aforementioned tissue lump as sampled from living body. 1) In the case where the above tissue lump has a size of not smaller than 3 mm cube, it is favorable to carry out the mechanical separation and enzymatic dispersion. 2) In the case where the above tissue lump has a size of 0.5 to 3 mm (but not including 3 mm) cube and smaller than 3 mm cube, the mechanical separation is not needed, but it is favorable to carry out only the enzymatic dispersion. 3) In the case where the above tissue lump has a size of smaller than 0.5 mm cube and is as small as a solid tissue portion that is not confirmed with the naked eye, neither the mechanical separation nor enzymatic dispersion may be needed. The further detailed treatment conditions of the above 1) to 3) are described in the below-mentioned examples of some preferred embodiments.

In the culturing process according to the present invention, the culture is favorably carried out on a surface of a supporting base, and the aforementioned supporting base favorably has a layer, including an extracellular matrix, as a cell adhesion factor. In the present invention, conventional culture methods (e.g. a monolayer culture method, a coated dish culture method, and a on-collagen-gel culture method) can favorably be employed. Among them, a two-dimensional monolayer culture method is favorably employed when the culture is carried out on the surface of the supporting base in the above way (when the culture is carried out in a state where the aimed cells are stuck on the surface of the supporting base). Specifically, a culture sample and a culture medium are placed in a culture container having the supporting base, and kept under definite environmental conditions, whereby only specific live cells containing the aimed animal cells (e.g. cancer cells) are proliferated under conditions where they are stuck on the surface of the supporting base of the culture container. At this time, such as apparatuses as used and treatment conditions are those as in such as conventional monolayer culture method.

It is favorable that the surface of the aforementioned supporting base comprises a material which allows the cells to favorably adhere and proliferate, or is coated with a single layer of a chemical substance or a cell adhesion factor, which allows the cells to favorably adhere and proliferate. Examples of this cell adhesion factor favorably include extracellular matrixes, such as various types of collagen, fibronectin, laminin, vitronectin, cadherin, gelatin, peptides, and integrin. These may be used either alone respectively or in combinations with each other. In view of further improving the cell adhesion and cell extension, various collagens are favorably used. Among the various collagens, a type-I or type-IV collagen is particularly favorably used.

Figure 13:
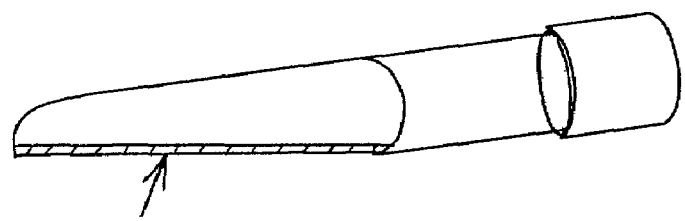
FIG. 13 is a partial perspective sectional view of a receptacle that is one example of the culture supporting base that can be used for the process for culturing animal cells according to the present invention.
Figure 14:
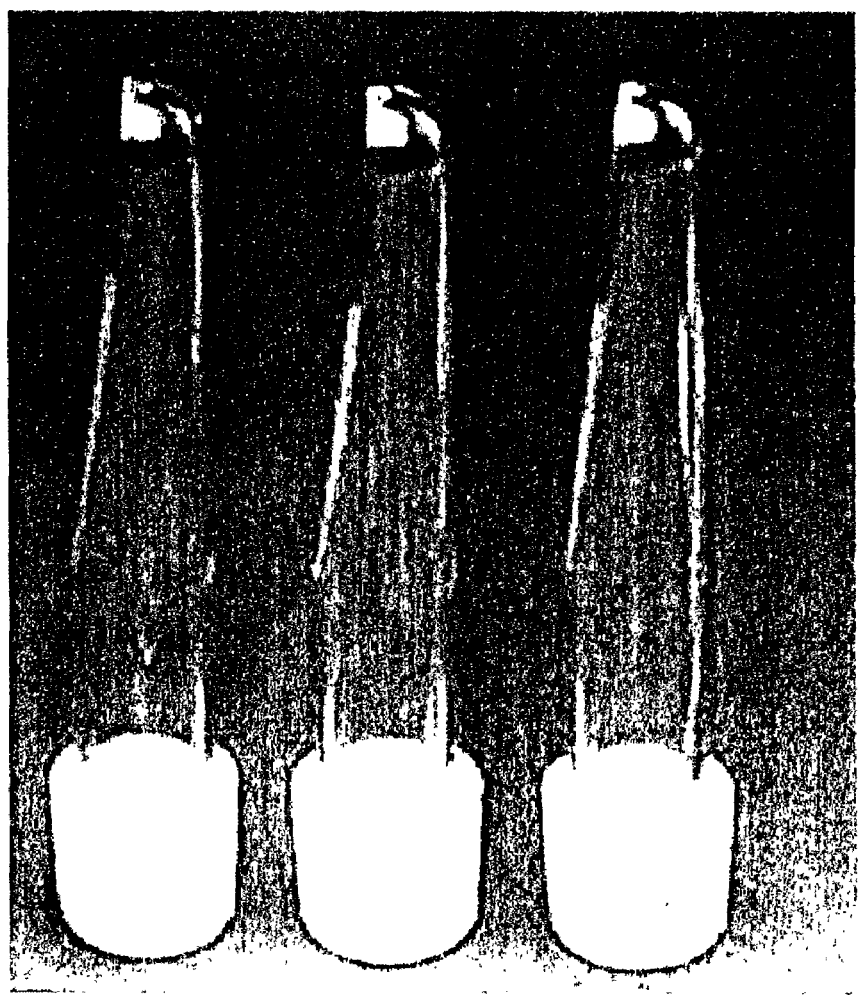
FIG. 14 is a photo of three containers as stood in a row wherein the container is one example of the culture supporting base that can be used for the process for culturing animal cells according to the present invention.

The shape of the culture container having the aforementioned supporting base is not especially limited, and it may be any shape. However, for example, a dish and a tube are favorable. The dish is not especially limited, but examples thereof favorably include: dishes for culturing cells, such as plastic dishes and glass-made Petri dishes; multiplates, such as micro wellplates or micro titerplates having such as 6, 12, 24, 48, or 96 wells; flasks for culturing cells; and culture plates, such as cover slips and cell disks. The tube is not especially limited, but examples thereof favorably include flat-bottomed or round-bottomed tube containers. Examples thereof more favorably include flat-bottomed tube containers obtained by cutting a portion of a tube as shown in FIGS. 13 and 14, so that the containers will have a moderately gentle angle to the central axis of the containers. Incidentally, the cutting face of the tube as shown in FIGS. 13 and 14 is a flat around-wall. Among the culture containers having the above exemplified shapes, the tube, especially the tube container having a shape as shown in FIGS. 13 and 14 is especially favorable at the following points. It has a surface shape and surface area of the around-wall which is fitted for culturing biopsy cells (In the present invention, when the "surface area" or "bottom area" is mentioned as to the supporting base, the area is defined as an area of a portion of sticking and culturing cells on the supporting base.), and besides has an excellent coatability of the cell adhesion factor. In addition, the sudden pH change of the culture medium can be suppressed. Therefore, the initial adhesion of the aimed cancer cells and the maintenance of the cell activity are excellent, and the tube can stabilize activities of antibiotic agents. Furthermore, living adhered cells can be collected by such as subjecting them exactly to centrifugal treatment, and thereby the high collection ratio can be achieved and the loss can be greatly decreased when the collection is carried out. Accordingly, for example, there are particularly advantages in that the culture having a high density can also be carried out in a very stable culture state.

The surface area of the aforementioned supporting base (area of a portion where cells are stuck and cultured) is favorably in the range of 0.01 to 25.0 $cm^2$, more favorably 0.5 to 10.0 $cm^2$, still more favorably 2.0 to 6.0 $cm^2$. In addition, as to the tube container as shown in FIGS. 13 and 14, the area of the aforementioned cutting face to be a flat face is particularly favorably 5.5 $cm^2$, and various excellent effects when this tube container is used can remarkably be displayed. In the case where the surface area of the aforementioned supporting base is smaller than 0.01 $cm^2$, it is difficult to seed cells onto the supporting base and it is limited to proliferate cells. In addition, in the case where the surface area of the aforementioned supporting base is larger than 25.0 $cm^2$, the cell density is lowered when the cells-seeding is carried out, and the interaction between the cells does not act sufficiently. Therefore, the initial adhesion is lowered.

As is mentioned in the above way, when the culturing process according to the present invention is a culturing process carried out on the surface of the supporting base having the layer which includes the extracellular matrix as the cell adhesion factor, the unnecessary component which does not adhere to the surface of the supporting base can be removed in the culture sample, and only the live cells adhering to the surface of the supporting base can favorably be collected by removing the culture medium in the culture container after the culture. Particularly, such as tumor-dead cells, their lumps, lumps of fibroblast cells, undigested materials of enzymes, blood cells, and lymphocytes can favorably be removed. In the collection of live cells adhering to the surface of the supporting base, the means such as EDTA-trypsin treatment can be applied and is favorably carried out after the above monolayer culture method.

In addition, in the culturing process according to the present invention, a collagen gel layer can be used when the aforementioned culture is carried out on the gel. The material of the collagen gel layer may be the same collagen material to form the below-mentioned globular collagen gel. The thickness of the collagen gel layer may be such a thickness as not to directly stick the aimed animal cells (e.g. cancer cells) to the surface of the supporting base. The aimed animal cells (e.g. cancer cells) as adhered to the surface of the collagen gel layer can easily be separated from the surface of the supporting base by collagenase treatment, and then collected.

In this way, if the collagen gel layer is beforehand formed on the surface of the supporting base, and the culture sample including the aimed animal cells (e.g. cancer cells) is cultured, and only the live cells adhering to the surface of the collagen gel layer is collected by the collagenase treatment, the proliferation of the aimed animal cells (e.g. cancer cells) on the collagen gel is more favorably carried out than the culture in a state of directly sticking the animal cells (e.g. cancer cells) on the surface of the supporting base. The collagenase treatment damages little live cell when proliferated live cells are collected. This is because the collagen gel layer itself whereon the live cells stick are enzymatically decomposed prior to the action to the live cells in the collagenase treatment, and thereby they have little unfavorable influence upon the live cells.

The process for culturing an animal cell, according to the present invention, may be a culturing process including only the above-mentioned culture step, or a culturing process further including other various steps.

Although the culturing process further including other various steps is not especially limited, for example, favorable is a culturing process comprising: a preliminary culture step using the above-mentioned culturing process; a cells-seeding step subsequent to this preliminary culture step; an embedding step; and a proliferative culture step.

The aforementioned cells-seeding step is a step of dispersing the animal cells, which are contained in culture samples collected in the preliminary culture step, into a collagen solution.

The aforementioned embedding step is a step of placing the a droplet or droplets of the collagen solution, resultant from the cells-seeding step, on a surface of a supporting base material and allowing the droplet or droplets to gel to form and fix on the surface of the supporting base material a globular collagen gel having a convex surface.

The aforementioned proliferative culture step is a step of contacting the collagen gel, resultant from the embedding step, with a liquid as a culture medium and culturing the animal cells.

The culturing process may further comprise an evaluation step after the proliferative culture step.

As is mentioned in the above way, if the culture sample including the aimed animal cells (e.g. cancer cells) is beforehand cultured on a surface of other supporting base in the preliminary culture step, and even if the cell number (absolute amount) of the aimed animal cells (e.g. cancer cells) as obtained by sampling from a living body is small, the cell number can sufficiently be increased and maintained due to the above-mentioned effects. Accordingly, even if the number of the test as desired to carry out after the culture is large and the division of the cell number is necessary, the sufficient number of the aimed animal cells (e.g. cancer cells) can be embedded in the globular collagen gel for each test. Therefore, a more correct test having a higher success rate can be carried out.

Hereinafter, the aforementioned cells-seeding step, embedding step, proliferative culture step, and evaluation step are specifically explained.

[Cells-seeding Step]:

A collagen solution used for forming the globular collagen gel(s) may contain a common collagen material conventionally used in various animal cell-embedded culture methods, a high-molecular material such as polysaccharides and other extracellular matrices, and a liquid material. For example, the collagen used is favorably acid-soluble type-I collagen. Various components other than collagen, which are necessary for culture, may also be added to the collagen solution. The collagen solution preferably has the composition of a buffer solution to match with or approximate to physiological conditions of the aimed animal cells (e.g. cancer cells). As to the cancer cells, the solution is favorably buffered to a pH of 6.2 to 7.6, more favorably 6.8 to 7.4, while the ionic strength is favorably set within the range of 100 to 180 mmols, more favorably 140 to 160 mmols. Conventional methods may be applied for mixing the culture sample into the collagen solution. The density of the aimed animal cells (e.g. cancer cells) to seed into the collagen solution is favorably in the range of about $10^2$ to about $10^7$ cells/ml. Especially for the primary culture such as the culturing process according to the present invention, the density is favorably in the range of about $10^3$ to about $10^6$ cells/ml.

The collagen concentration and the viscosity of the collagen solution influence the structure of the later-mentioned globular collagen gel. The specific quantitative conditions vary dependently on conditions such as the purpose of the test, but the collagen concentration is favorably in the range of 0.1 to 2.0 wt. %. In the case where the concentration is too high, the viscosity as mentioned below is high. On the other hand, in the case where the concentration is too low, the globular shape is difficult to maintain. The viscosity is favorably in the range of 50 to 2,000 centipoise, more favorably 100 to 1,000 centipoise. In the case where the viscosity is too low, the cells precipitate in the collagen solution, come into contact with a surface of the supporting base material, and proliferate in the form of a monolayer, thus making it impossible to make an accurate evaluation of various effects in tests after the culture, such as effects of anticancer agents. On the other hand, in the case where the viscosity is too high, the collagen solution is difficult to handle. In addition, the gel strength upon gelation of the collagen solution also affects the performance, and therefore the collagen as used preferably has a gel strength in the range of about 50 to about 1,000 g, more favorably in the range about 50 to about 700 g, and still more favorably in the range 100 to 500 g. The value of the gel strength is that measured according to JIS. In the case where the gel strength is too low, the globular collagen gel peels off from a surface of the supporting base material during tests, or the gel tends to contract. On the other hand, the gel strength is too high, the proliferation of the aimed animal cells (e.g. cancer cells) is inhibited.

[Embedding Step]:

The aforementioned supporting base material is not limited with its material and structure so long as it has a surface capable of fixing a collagen gel thereto. Examples of the usable supporting base material include culture dishes such as Petri dishes and multidishes, flasks, and other conventional culture containers. In addition, examples of the usable supporting base material further include culture plates such as glass or plastic cover slips and cell disks. The surface of the supporting base material is usually smooth and flat, but lines including frame-forming ridges and grooves to control the spread of the placed droplet of the collagen solution may also be formed on the surface of the supporting base material. It is favorable that these culture containers and supporting base materials are optically transparent.

If a droplet or droplets of the collagen solution containing a dispersed culture sample is placed on a surface of the supporting base material, such as the surface tension of the collagen solution acts to form a water-like droplet or droplets on the surface of the supporting base material. As a result, a globular collagen gel or gels with a spherical convex surface can be formed on the surface of the supporting base material.

The shape of the globular collagen gel differs depending on factors such as the viscosity and temperature of the droplet of the collagen solution which is placed, the amount of each droplet of the collagen solution which is placed, the wettability of the surface of the supporting base material, and other conditions. In addition, it is preferable to set the gel to the desired shape depending on the test method to be employed including, for example, photography conditions when photographing the globular collagen gel for the image analysis.

As to modes of placing the globular collagen gel on the supporting base material, one or more droplets of one collagen gel may be placed, or each droplet of at least two collagen gels may be placed. In addition, when the at least two collagen gels are cultured simultaneously, the gels may be in contact with each other on their partial or entire interface.

If the globular collagen gel having a convex surface is used, the globular collagen gel has a much smaller volume than a layered collagen gel, and thus, even when only a small amount of cancer cells is obtained from living body tissue, the cells can be seeded to a suitable and sufficient density. In addition, a wide area of the convex surface comes into contact with the culture medium, thus allowing for very efficient uptake of nutrients by the cells and excretion of waste from the cells. Furthermore, if the size of the culture container is selected, the amount of the culture medium coming into contact with the collagen gel can relatively be increased. The culture method of the present invention far more greatly improves the cell proliferativity than conventional methods in which a collagen gel layer is formed over the entire internal bottom of a culture dish and nutrient and waste are exchanged only at a flat surface of the collagen gel layer.

In addition, the globular collagen gel is firmly fixed onto a surface of a supporting base material, because the globular collagen gel is formed by placing a droplet or droplets of a collagen solution containing the aimed animal cells (e.g. cancer cells) onto the surface of a supporting base material such as a culture dish, and then gelating the droplet(s). Consequently, results of culturing the aimed animal cells (e.g. cancer cells) may be observed or photographed while more easily specifying positions of the cells after culturing than results obtained by culturing in a layered collagen gel. In addition, the method for placing a droplet or droplets of the collagen solution, for example, may include dropping the collagen solution from above the surface of the supporting base material, or gently placing the collagen solution into the form of a globular water-like droplet or droplets using a pipette near the surface of the supporting base material.

Specifically, under normal test conditions, the size of each globular collagen gel is made to be in the range of 3 to 300 µl, favorably 3 to 150 µl, in terms of the volume of a droplet of the placed collagen solution. For practical use, it is favorably in the range of 5 to 100 µl, more favorably about 15 to about 50 µl. As is in the culturing process according to the present invention, if primary cells are cultured, the gel is favorably about 30 µl. In addition, the height of the globular collagen gel is favorably adjusted to about not more than 2 mm. The number of the formed collagen gel globules and their placing intervals on the surface of the supporting base material may optionally be varied as desired to match the measurements of the globular collagen gel and the structure of the supporting base material.

Collagen gels as used for microscopic observation and image analysis have needed to have a high transparency hitherto. However, in the process according to the present invention, collagen gels even with a relatively low transparency can be used. Specifically, collagen gels with a transmittance of 1 to 95% for 400 nm light can be used.

A test even using collagen gels with a low transmittance within the above-mentioned range can satisfactorily be carried out without being affected by turbidity if the collagen gels are subjected to the below-mentioned stain treatment.

Samples as mixed into the globular collagen gel may be various cells, such as cancer cells and normal cells, and besides may be compounds which act on the cells, for example, calcium, inorganic salts such as calcium phosphate, lipids, carbohydrates, and proteins.

[Proliferation Culture Step]:

The formed globular collagen gel needs to be kept in a gel state at least until the culture finishes. Even a three-dimensional globular collagen gel becomes flat and dry if it loses moisture due to drying. Once it is dried, it is difficult to restore to its original three-dimensional shape even if it is brought into contact with water. Thus, the globular collagen gel is preserved, after its formation until supplying such as the culture, so that it may not excessively dry. So long as the globular collagen gel is in contact with the culture medium, there is no possibility that the gel may be dried. After the completion of the culture, the fixing and drying of the globular collagen gel presents no problem for evaluating culture results.

If a culture container having the supporting base material is such as a culture dish, the culture medium may be brought into contact with a surface of the supporting base material by simply pouring the culture medium into the container to cover the surface of the supporting base material. If a culture container having the supporting base material is a culture plate, the culture medium may be poured in under conditions where the culture plate is placed in another culture container.

Although the culture medium usable in the proliferative culture step is not especially limited, it may fitly be selected from various known culture mediums depending upon test conditions. However, the culture medium is favorably has such a composition as is suitable for proliferating the aimed animal cells (e.g. cancer cells) and can suppress the proliferation of other cells. In the present invention, for example, it is favorable that the culture medium is a culture medium as used in the preliminary culture step.

The amount of the culture medium as used in the proliferative culture step is enough to cover the globular collagen gel for a satisfactory degree of culturing. In the case where the number of the aimed animal cells (e.g. cancer cells) as embedded in the globular collagen gel is large, the amount of the culture medium needs to be increased or the intervals of exchanging the culture medium during the culture needs to be shortened.

In addition, in the case where interactions of cells are observed in such as co-culture tests, a collagen layer which contains tested cells instead of the culture medium can be placed in the layered form over the entire container, or a globular collagen in which other cells are dispersed can be placed in the same culture container.

The culture in the proliferation culture step is favorably carried out by keeping the culture medium in contact with the globular collagen gel as fixed to the surface of the supporting base material, for a definite period of time under environment conditions such as in a thermostat incubator or a $CO_2$ incubator. In order to such as test the sensitivity to an anticancer agent after the culture, it may be brought into contact with the globular collagen gel as fixed to the surface of the supporting base material, at an appropriate stage before or during the culture. Examples of the favorable method thereof include a method in which the anticancer agent is added to the culture medium, or a method in which the culture medium is exchanged with a culture medium to which the anticancer agent is added. Procedures and conditions for bringing the anticancer agent into contact with the collagen gel may be optional. In addition, when effects of agents other than the anticancer agent are tested, such agents may be brought into contact with the collagen gel in the same manner as the anticancer agent. When effects of a change of temperature, for example, by heating, or effects of radiations or the like are tested, the globular collagen gel may be exposed under those environment conditions for a definite period of time.

[Evaluation Step]:

Depending on culture conditions, the aimed animal cells (e.g. cancer cells) in the globular collagen gel are proliferated or dead after the completion of the culture. Means of evaluation as in conventional culture methods may be applied in order to evaluate culture results, such as the proliferation state of the aimed animal cells (e.g. cancer cells). For example, the number of the formed colonies or cells may be counted by visual observation using a microscope, or an image obtained by photographing or imaging may be analyzed. Various characteristics of the aimed animal cells (e.g. cancer cells) existing there may be observed and evaluated while the globular collagen gel is fixed to the surface of the supporting base material.

When the image analysis is carried out as a method for evaluating culture results, such as the placement form of the globular collagen gel on the surface of the supporting base material or the structure of the culture container is set so as to facilitate the photographing and image analysis. A supporting base material with the aforementioned lines including ridges and grooves to restrict the shape is favorably used in order to precisely set the shape and position of the globular collagen gel on a surface of the supporting base material. The images of the aimed animal cells (e.g. cancer cells) and their colonies can be distinguished from other images such as of fibroblast cells by utilizing image analysis in which photographed images are electronically processed and analyzed using such as a computer, thus the proliferation state of the aimed animal cells (e.g. cancer cells) can accurately be evaluated, because cells as cultured under embedded conditions in the globular collagen gel show specific proliferation morphology.

After culturing using the globular collagen gel, if only live cells in the globular collagen gel are selectively stained and if its results are evaluated, then live cells can accurately be distinguished from dead ones in the aimed animal cells (e.g. cancer cells), thus allowing an accurate evaluation of the proliferation state of the aimed animal cells (e.g. cancer cells) being studied in the culture test. The stain method may be a conventional method for staining various cells, so long as it is a method capable of selectively staining live cells as distinct from other substances including dead cells. Particular staining agents and staining conditions may be according to conventional methods. For example, NR stain methods or latex particle stain methods in which phagocytic activity of cells is utilized, SDI methods or FDA stain methods in which enzyme activity in cells is utilized, or other stain methods using a fluorescent reagent, or the like may be used.

An example of the treatment for selectively staining only live cells is an NR stain treatment, which uses NR (neutral red) stain as the staining agent. Stain conditions may be the same as in conventional NR stain. In this NR treatment, if a pigment is fixed into cells and if the globular collagen gel is then dried, the dried globular collagen gel reflecting culture results by the stained state can be preserved for a long time, and the procedure of evaluation such as by image analysis provide the same accurate analysis whenever the evaluation procedure may be made. NR stain is a preferable method for selectively staining only live ones of the aimed animal cells (e.g. cancer cells), but if left to stand after staining, an NR-staining agent as incorporated into live cells elutes within a short period, thus making an evaluation impossible except just after staining. If then, as mentioned above, the pigment is fixed into cells by such as formalin fixation, it becomes possible to temporarily prevent elution of the staining agent. If the globular collagen gel is then washed with water and dried, there is no possibility of degeneration or degradation. Means for drying, for example, may be water-absorption using filter paper, air-drying, or forcible drying by heating to a range of about 10 to about 50° C. The dried collagen gel prepared by removing the moisture from the globular collagen gel has a flat, sheet-like structure. The dried globular collagen gel can successfully be sealed using sealants such as Crystal/Maunt (produced by Biomeda).

In addition, in the case where image analysis is performed, the photography procedure is much easier by setting the focus on the aimed animal cells (e.g. cancer cells) in a flat, dry collagen gel rather than on the aimed animal cells (e.g. cancer cells) in a three-dimensional, globular collagen gel, allowing a more focused image and thus a more accurate evaluation of culture results.

FDA stain treatment is another treatment for selectively staining only live cells. This treatment is a method including measuring fluorescent coloring as produced by a reaction of an FDA (Fluorescein Di Acetate) staining agent upon live cells followed by exposure to excitatory light. Basic apparatuses and conditions for tests may be the same as in conventional FDA stain methods, but in the present invention the irradiation amount of excitatory light and the measurement environment temperature are set to within the ranges given later. The in-vivo-like morphology of colonies that fluorescently colored cells form in the globular collagen gel can be quantified and evaluated by image analysis. The FDA stain method is a method which allows satisfactory selective stain of only live ones of the aimed animal cells (e.g. cancer cells). However, since conventional FDA stain methods include irradiating relatively strong excitatory light or carrying out the measurement at about normal temperature, these methods have disadvantages, for example, in that the activity of the aimed animal cells (e.g. cancer cells) is lowered. However, such disadvantages may be reduced if the irradiation amount and the temperature conditions are kept within the ranges given below. As a result, prior to culturing the aimed animal cells (e.g. cancer cells) or at any stage during the culture, the evaluation of the culture state by an FDA stain method, and thereafter the continuation of the culture can be carried out. In other words, the continuous evaluation of the culture state can be carried out. In particular, if the culture method under embedded conditions in the globular collagen gel is combined with the evaluation method utilizing image analysis, a highly precise measurement and evaluation can be made even under conditions where the irradiation amount of excitatory light is small and where the fluorescent coloring is weak, thus such a combined method is preferred.

The conditions for measurement after the FDA stain are as follows: the irradiation amount of excitatory light is in the range of $1\times10^0$ to $1\times10^7$ lux sec, favorably $1\times10^1$ to $1\times10^5$ lux·sec, and the measurement environment temperature in the range of 1 to 15° C., favorably 8 to 12° C.

If the calorimetric analysis as another method for evaluating culture results is carried out using a coloring reagent which selectively causes a color reaction due to metabolic activity of live cells as embedded in the globular collagen gel, then culture results can comparatively easily be evaluated even without using complicated equipments such as image analyzers. The accuracy of the evaluation is sufficient in practical application, particularly if a culture sample with little contamination by fibroblast cells, or an established cell line, is used as a culture sample or if the contamination or proliferation of the fibroblast cells is suppressed in any of the various manners as mentioned above. In addition, if the coloring agent is soluble in water, the evaluation can continuously be carried out, because the water-soluble coloring agent gives no unfavorable affection to the animal cells (e.g. cancer cells) as same as the FDA stain.

Specific methods and conditions for the step including the aforementioned calorimetric analysis may be the same as in culture tests for other cells. Examples of the coloring reagent as used include an AB coloring reagent (trade name: Alamar Blue, produced by Alamar Bioscience Co., Ltd.), a WST-1 coloring reagent, an XTT coloring reagent and a MTT pigment reductant.

As a method in which the measurement can be carried out even if cells are dead, there is a method including selectively staining substances as contained in cells in the globular collagen gel, thus evaluating results. The stain methods as employed may be a variety of conventional biochemical stain methods so long as they allow the selective stain of substances as contained in cells. Specific staining agents and conditions may be conventional ones, for example, staining reagents as used for staining tissue can be used.

Specific examples of the staining agents include hematoxylin, Giemsa's solution, pigments such as Crystal Violet, ethidium bromide which stains nucleic acid, reagents which stain components such as proteins, carbohydrates and lipids, reagents which stain substances in cell membranes, reagents which stain specific parts such as cytoskeletons, antibodies against specific antigens, DNA probe.

If substances as contained in cells in the globular collagen gel are selectively stained and if its results are evaluated, the productivity of specific substances from cells can clearly be distinguished whether the cells are alive or not, thus the proliferation state of the animal cells (e.g. cancer cells) which are objects of culture tests can accurately be evaluated from the substance productivity of the cells.

In addition, live cells or cell components can be stained doubly or triply. Various actions of cells can be evaluated for an identical sample by multiple staining of the cells.

Furthermore, the globular collagen gel may be separated from the surface of the supporting base material, for example, by dissolving the gel, thus evaluating culture results.

An example of the methods is a method including: quantitatively analyzing substances as contained in cells in the globular collagen gel; and evaluating its results. The quantitative-analysis methods as employed may be a variety of conventional biochemical ones so long as they allow quantitative analysis of substances as contained in cells. Specific methods for quantitative analysis may be in accordance with conventional ones, for example, a commassie brilliant blue color method or Lowry method for quantitatively analyzing proteins, a DABA fluorescent coloring method for quantitatively analyzing nucleic acid, a luciferin luminescence method for measuring ATP, or various methods for quantitatively analyzing carbohydrates.

If substances as contained in cells in the globular collagen gel are quantitatively analyzed and if its results are evaluated, the productivity of specific substances from cells can clearly be distinguished whether the cells are alive or not, thus the proliferation state of the animal cells (e.g. cancer cells) which are objects of culture tests can accurately be evaluated from the substance productivity of the cells.

In addition, another method includes quantitatively analyzing substances as secreted from cells in the globular collagen gel to a culture medium, and evaluating its results. The quantitative analysis methods as employed may be a variety of conventional biochemical ones so long as they allow quantitative analysis of substances as secreted from cells. Specific methods for quantitative analysis may be in accordance with conventional ones, for example, various methods such as methods for quantitatively analyzing lactic acid and the like which are typical metabolic products (waste).

If substances as contained in cells in the globular collagen gel are quantitatively analyzed and if its results are evaluated, the productivity of specific substances from cells can clearly be distinguished whether the cells are alive or not, thus the proliferation state of the animal cells (e.g. cancer cells) which are objects of culture-tests can accurately be evaluated from the substance productivity of the cells.

The kit for culturing animal cells, according to the present invention, comprises the following constituent articles: a collagen solution; a concentrated culture medium; a reconstituting buffer solution; an enzyme for dispersing cells; a tube for a culture supporting base, a culture medium for preliminary culture; a serum-free culture medium, and a cell-dyeing agent.

The kit for culturing animal cells, according to the present invention, can favorably be used for carrying out the aforementioned process for culturing animal cells according to the present invention.

Hereinafter, the aforementioned respective constituent articles are explained with citing specific examples.

The collagen solution is not especially limited, but specific examples thereof favorably include acid-soluble type-I or type-IV collagens, or pepsin-soluble type-I or type-III collagens. Among them, the acid-soluble type-I collagens are more favorable.

The concentrated culture medium is not especially limited, but specific examples thereof favorably include culture fundamental medium for mammalian cells, such as McCoy's 5A, RPMI-1640, D-MEM, MEM, MCDB-131, Ham's F-12, D-MEM/F-12, and Medium-199. Among them, the Ham's F-12, D-MEM, and D-MEM/F-12 are favorable.

The reconstituting buffer solution is not especially limited, but specific examples thereof favorably include phosphoric-acid buffer solutions of which the pHs are adjusted to around pH 7.4, more favorably a 50 mM-NaOH solution containing 260 mM-sodium bicarbonate and 200 mM-HEPES, as used in Example 1 below.

The enzyme for dispersing cells is not especially limited, but specific examples thereof favorably include collagenase, pronase, trypsin, dispase, elastase, hyaluronidase, mucinase, and DNase. Among them, more favorable is a complexed enzyme including such as the collagenase, dispase, elastase, hyaluronidase, and DNase.

The tube for a culture supporting base is favorably the above-mentioned tube container as shown in FIGS. 13 and 14.

The culture medium for preliminary culture is not especially limited, but specific examples thereof favorably include culture mediums obtained by adding fetal bovine serum (FBS) to Ham's F-12, D-MEM, or a D-MEM/F-12 mixed solution so that the concentration of the fetal bovine serum will be in the range of 5 to 20%, and culture mediums obtained by further adding various growth proliferation factors to this culture, more favorably culture mediums containing such various antibiotics as mentioned in Example 1 below, in these culture mediums.

The serum-free culture medium is not especially limited, but specific examples thereof favorably include culture mediums obtained by adding various growth proliferation factors to Ham's F-12, D-MEM, or a D-MEM/F-12 mixed solution, more favorably culture mediums containing such various antibiotics as mentioned in Example 1 below, in these culture mediums.

The cell-dyeing agent is not especially limited, but specific examples thereof favorably include Neutral Red, Trypan Blue, Alamar Blue, Giemsa, Crystal Violet, FDA, and MTT reagents. Among them, more favorable is the Neutral Red which utilizes phagocytosis-to lysosome and has high correlation to cell life.

The kit for culturing animal cells, according to the present invention, may comprise other constituent articles other than the aforementioned constituent articles, and they are not especially limited. Specific examples thereof favorably include medical or curative medicines, such as washing liquids or preserving liquids for biological tissue (e.g. culture sample as mentioned in the present invention), anticancer agents, anticancer-action promoters, inhibitors for angiogenesis, inhibitors for cancer metastasis, and anti-hormone agents.

(Effects and Advantages of the Invention):

The present invention can provide a novel process for culturing animal cells, in which, even if the number of cells as sampled for biopsy is extremely small, the proliferation can sufficiently be maintained so as to enable to carry out various tests, and the contamination with bacteria can be inhibited without damaging physiological activity of cells.

DETAILED DESCRIPTION OF PREFERRED EMBODIMENTS

Hereinafter, the present invention is more specifically illustrated by the following examples of some preferred embodiments. However, the present invention is not limited thereto.

EXAMPLE 1

<<Anticancer Agent Sensitivity Test>>

Various cancer cells (various cancer cells as oriented from different organs), which were cells as sampled for biopsy, were subjected to an anticancer agent sensitivity test by the collagen gel-embedded culture method following the procedure as shown in the flow sheet of Table 1. Used as the cancer cells subjected to the test were breast cancer cells, lung cancer cells, colon cancer cells, and pancreatic cancer cells.

Regarding the various cancer cells, there were determined the success number and success rate of the primary culture to the number of the performed tests, and further, only those of which the primary culture had succeeded were taken as the subjects to carry out the anticancer agent sensitivity test to determine the success number and success rate of the anticancer agent sensitivity test to the success number of the primary culture. Their results are shown in Table 2. The primary culture means the preliminary culture step as also shown in the flow sheet of Table 1.

In addition, shown in Table 3 from the viewpoint of the success or failure of the primary culture are, as to the success cases of the primary culture, as follows: they are the numbers of success cases (cases where evaluation was possible) and failure cases (cases where evaluation was impossible due to insufficient cell proliferation) of the subsequent anticancer agent sensitivity test, and further as to the failure cases of the primary culture, as follows: the numbers of cases where it was impossible for cells to proliferate and cases where contamination was caused by such as unwanted bacteria.

Incidentally, as to the culture medium as used in each step in Example 1, there is used a culture medium as prepared by adding various antibiotic agents (penicillin, kanamycin, fungizone, vancomycin) to the following basal medium.

Basal Medium:

DF culture medium (DF: a mixed culture medium containing one volume of Dulbecco modified Eagle (DME) culture medium and one volume of Ham's F12 culture medium)+10% FBS (FBS: fetal bovine serum)+5 µg/ml insulin (product of Sigma Co.)+10 ng/ml EGF (product of Collaborative Co.; EGF (epidermal growth factor))+20 ng/ml hydrocortisone (product of Sigma Co.)

Penicillin, Kanamycin:

Two 1 g-vials of penicillin (product of Toyama Chemical Co., Ltd.; for penicillin injection) and 1 g potency of kanamycin (product of GIBCO BRL Co., Ltd.; sulfuric acid kanamycin reagent) are dissolved into 20 ml of PBS, and the resultant solution is added to the basal medium in such an amount as gives a concentration of 1% (final concentration of penicillin=1 mg/ml; final concentration of kanamycin=0.5 mg/ml) on the basis of the basal medium.

Fungizone:

Amphotericin B (product of Dainippon Pharmaceutical Co., Ltd.) of 250 µg/ml is added to the basal medium in such an amount as gives a concentration of 1% (final concentration=2.5 µg/ml) on the basis of the basal medium.

Vancomycin:

An amount of 1 g of vancomycin hydrochloride (product of Wako Pure Chemical Industries, Ltd.) is dissolved into 10 ml of FBS, and the resultant solution is added to the basal medium in such an amount as gives a concentration of 2% (final concentration=2 mg/ml) on the basis of the basal medium.

TABLE 1

<<Anticancer agent sensitivity test flow sheet>>

(1) Sampling of test materials (biopsy tumor tissue)
↓
(2) Separating and dispersing treatments of cells
↓
(3) Preliminary culture step (proliferation and collection of live cells)
↓
(4) Cells-seeding step for collected cells (preparation of collagen solution)
↓
(5) Step of embedding a globular collagen gel
↓
(6) Proliferative culture step (proliferation of cells and contact with anticancer agent)
↓
(7) Evaluation step (staining and fixing of cells, and analysis of image)

The following is a detailed explanation about each item of the flow sheet of Table 1.

[Test Materials]:

As the test materials, biopsy materials are taken out of human cancer patients' tissue of breast cancer, lung cancer, colon cancer, and pancreatic cancer by a low invasive sampling method.

[Separating and Dispersing Treatments]:

Immediately after the sampling, the biopsy materials (biopsy cells) are suspended into the above culture medium and then subjected to the below-mentioned separating and dispersing treatments. Incidentally, in these treatments, the above culture medium is fitly used.

In the following way, the separating and dispersing treatments of cells ((1) to (8)) are carried out according to states A) to C) of tissue lumps of the biopsy materials (collected biopsy tumor tissue). These treatments enable reducing the loss in number of cells when collecting cells prior to the preliminary culture step.

(States of Tissue Lumps):

A) In the case where the tissue lumps are not smaller than 3 mm square, mechanical separation and enzymatic dispersion are needed, thus performing the treatments (1) to (8) below.

B) In the case where the tissue lumps are 0.5 to 3 mm square (but not including 3 mm), mechanical separation is unneeded, and enzymatic dispersion is needed, thus performing the treatments (1) and (4) to (8) below.

C) In the case where the tissue lumps are smaller than 0.5 mm square, both mechanical separation and enzymatic dispersion are unneeded, thus performing either the treatments (1) and (7) to (8) below or only the treatment (8) below.

(Separating and Dispersing Treatments of Cells):

(1) After the sampling, the biopsy materials are collected into a centrifugal tube of 15 ml containing 12 ml of the aforementioned culture medium, and then centrifugal separation (1,400 rpm, 3 minutes) is performed, and then the precipitated tumor tissue is collected.

(2) The centrifugally collected tumor tissue is suspended into 5 ml of the culture medium and then moved onto a dish of 6 cm.

(3) Only solid tissue is separately moved onto a dish of 10 cm and then minced with a razor so as to be pasty, and solids are beforehand separated so that the enzymatic treatment can rapidly be carried out, and then the residue is collected into a centrifugal tube of 15 ml, and then centrifugal separation is performed at 1,400 rpm, for 3 minutes. Incidentally, in the case where many isolated cells are observed in the culture medium as used in the above treatment (2), they are separately collected into a centrifugal tube and then subjected to the preliminary culture step directly without performing any enzymatic treatment.

(4) A 0.1% enzymatic treatment solution is added to the centrifugally collected precipitate, and then they are shaken at 37° C. with a mild mixer for 30 to 60 minutes to carry out enzymatic dispersion of cells (digestion of intercellular interstitial tissue). Incidentally, the state of the dispersion is fitly observed with a microscope. The shaking time is set properly every original organ. Incidentally, the 0.1% enzymatic treatment solution was prepared by diluting a multi-enzyme complex, containing collagenase (product of Nitta Gelatin Inc.), hyaluronidase (product of Sigma Co.), dispase (product of Godo Shusei Co.), elastase (product of Wako Pure Chemical Industries, Ltd.) and DNase (product of Sigma Co.), to 0.1% with the DF culture medium solution.

(5) Immediately after the enzymatic treatment, the volume is increased with the culture medium to stop the enzymatic reaction, and then centrifugal collection is performed at 1,400 rpm, for 3 minutes.

(6) An amount of 1 to 2 ml of EGTA-Trypsin is added to the centrifugally collected precipitate to perform the treatment for 3 to 5 minutes, thereby dispersing cells.

(7) Cells suspending is strongly carried out with the culture medium to mechanically loosen cells. (In the case where the state of the tissue lumps is A) above, a separating operation is carried out with a nylon mesh filter (φ300 µm).) Then, centrifugal separation is performed at 1,400 rpm, for 3 minutes, and further, a density gradient centrifugation method is used to remove blood cell components and a portion of fibroblast cells.

(8) Cells in the centrifugally collected precipitate are seeded onto a beforehand prepared culture supporting base and then subjected to the preliminary culture step with the above culture medium.

[Preliminary Culture Step]:

A tubular plastic container having a surface area of 5.5 cm$^2$ was used as a supporting base in the preliminary culture step wherein a type-I collagen gel (or type-IV collagen gel) had been coated as an extracellular matrix onto a surface of the container before the use. The dispersion containing various cancer cells (including such as live tumor cells, fibroblast cells, dead tumor cells, dead tumor cell lumps, and enzymatically undigested substances), as obtained by the above dispersing and separating treatments, was seeded onto the collagen gel, and then the culture was performed with the above culture medium in a 5% $CO_2$ incubator of 37° C.

When the dispersion solution containing such as cancer cells was preliminarily cultured in the above way, it was seen that only the live cells adhered to and spread on the surface of the supporting base. Specifically, when microscopic observation was performed just after the culture and 24 hours later than the culture, it was seen that: the live cells adhered to and spread on the collagen gel, while the cancer-dead cells, the cancer-dead cell clumps, and the enzymatically undigested substances were floating without adhering to the collagen gel. Thereafter, the culture medium was sucked, and the surface of the supporting base was washed. When microscopic observation was performed in this state, the cancer-dead cells, the cancer-dead cell clumps, and the enzymatically undigested substances were removed, and there were seen only the live cells which had adhered to and spread on the collagen gel.

[Cells-Seeding Step]:

The live cells which had adhered to and spread on the collagen gel were detached by collagenase treatment, and then such as live tumor cells were collected by centrifugal separation.

Incidentally, in the above preliminary culture, the cells were detached from the supporting base basically after 24 hours and then collected, but in the case where only a small number of live tumor cells adhered alive to the surface of the supporting base, when the preliminary culture time was extended (e.g. to about 2-7 days) to perform the culture the live tumor cells could sufficiently be proliferated in the stage of the preliminary culture. In other words, even if only a small number of live tumor cells were obtained, the live tumor cells could be proliferated by the preliminary culture and then transferred to the subsequent step. Incidentally, in the case where there is a possibility of the extension of time, specifically, in the case where the culture is performed for a long time of not less than 3 days, the type-I collagen gel is preferable to the type-IV collagen gel as the extracellular matrix being coated onto the surface of the supporting base.

[Embedding Step]:

The live tumor cells as obtained by the above-mentioned preliminary culture and collection steps were embedded into a globular collagen gel and cultured.

The embedded culture was carried out as follows: 1 volume of 10-fold concentrated Ham's F12 culture medium (sodium bicarbonate-free) and 1 volume of a reconstituting buffer solution (50 mM NaOH solution containing 260 mM sodium bicarbonate and 200 mM-HEPES) were added to 8 volumes of Cellmatrix Type-CD (0.3% acid-soluble Type-I collagen solution: product of Nitta Gelatin Inc.); and then the cancer cells as obtained in the aforementioned preliminary culture and collection steps were added and well mixed into the resultant mixture; and then the final concentration was adjusted to $1 \times 10^5$ cells/ml; and then the resultant mixture was preserved in ice.

Next, this collagen mixture solution was placed in hemispherical form onto 3 droplets of a 6-well multiplate at a rate of 30 μl/well using a micropipette and gelled to prepare a globular collagen gel.

A 3.0-ml portion of the culture medium containing anti-cancer agents was superposed on the globular collagen gel in which the cancer cells were embedded and which was obtained in the embedding step, and then the cancer cells were contacted with the anticancer agents by keeping them in a 5% $CO_2$ incubator of 37° C. for 24 hours. Used as the anticancer agents were such as Taxol, Taxotere, Epi (Epirubicin), NVB (Navelbine), MMC (mitomycin C), CDDP (cisplatin), VDS (vindesine), VP-16 (etoposide), 5-FU (5-fluorouracil) and ADM (adriamycin).

Then, the culture medium containing the anticancer agents was removed by suction, and then 3.0 ml of an anticancer agent-free culture medium was instead added, and then the resultant mixture was shaken in a 5% $CO_2$ incubator, thus washing the globular collagen gel. This procedure was repeated at least every 15 minutes for a total of 3 times, whereby the anticancer agents were removed from the globular collagen gel.

[Proliferative Culture Step]:

After the above agent contacting and removing steps, 4 ml of a culture medium was added, and then the culture was effected in a 5% $CO_2$ incubator of 37° C. for 7 days. The culture medium was exchanged as the need arose. The above culture medium was used as the aforementioned culture medium.

[Evaluation Step]:

The neutral red (NR) stain method was used. In detail, the culture medium was exchanged with a culture medium to which an NR-staining agent had been added (NR concentration: 25-50 μg/ml), and then shaking was effected for 2 hours in a 5% $CO_2$ incubator of 37° C., thus incorporating the NR into the cells.

After the treatment by the NR stain method, the culture medium containing the NR was exchanged with PBS (Phosphate Buffered Saline), and then the sample was allowed to stand stationary in a room for 10 minutes, thus removing the NR remaining outside of the cells.

Next, the PBS was exchanged with neutral buffered 10% formalin, and then the sample was allowed to stand stationary in a room for 40 minutes, thus fixing the cells and the NR as incorporated into the cells.

The globular collagen gel to which the cells had been fixed was immersed in distilled water for 10 minutes, thus removing the salts. The globular collagen gel which had been displaced with the distilled water was air-dried at room temperature, whereby a flat dried product was formed. At this time, the cultured cells were fixed in the dried collagen gel while containing the NR. These fixed cells exhibit no discoloration and can endure even long-term preservation. The fixed cells were subjected to an image-analyzing treatment. Incidentally, for this image-analyzing treatment, there was used an image-analyzing method as disclosed in JP-A-15612/1998 (method for quantitative measurement of cancer cells).

TABLE 2

| Test materials Type of cancer | Number of performances | Primary culture Success number | Primary culture Success rate | Sensitivity test Success number | Sensitivity test Success rate |
|---|---|---|---|---|---|
| Example | | | | | |
| Breast cancer | 50 | 41 | 82.0% | 28 | 68.3% |
| Lung cancer | 25 | 14 | 56.0% | 12 | 85.7% |
| Colon cancer | 10 | 8 | 80.0% | 5 | 62.5% |
| Pancreatic cancer | 15 | 8 | 53.3% | 6 | 75.0% |
| Total | 100 | 71 | 71.0% | 51 | 71.8% |
| Comparative Example | | | | | |
| Breast cancer | 35 | 23 | 65.7% | 13 | 56.5% |
| Lung cancer | 18 | 6 | 33.3% | 3 | 50.0% |
| Colon cancer | 10 | 3 | 30.0% | 1 | 33.3% |
| Total | 63 | 32 | 50.80% | 17 | 46.6% |

TABLE 3

| Test materials Type of cancer | Number of performances | Success in primary culture Success in sensitivity test | Success in primary culture Failure in sensitivity test | Failure in primary culture NVC | Failure in primary culture Contami. |
|---|---|---|---|---|---|
| Example | | | | | |
| Breast cancer | 50 | 28 | 13 | 9 | 0 |
| Lung cancer | 25 | 12 | 2 | 11 | 0 |
| Colon cancer | 10 | 5 | 3 | 2 | 0 |
| Pancreatic cancer | 15 | 6 | 2 | 7 | 0 |
| Total | 100 | 51 | 20 | 29 | 0 |
| Comparative Example | | | | | |
| Breast cancer | 35 | 13 | 10 | 1 | 1 |
| Lung cancer | 18 | 3 | 3 | 11 | 1 |
| Colon cancer | 10 | 1 | 2 | 0 | 7 |
| Total | 63 | 17 | 15 | 22 | 9 |

Notes):
LGR: Low-growth-rate
NVC: Non-viable-cells
Contami.: Contamination

<<Antibacterial Test for Culture Medium>>

The following antibacterial test was carried out so as to additionally confirm the killing action (bactericidal action) and the multiplication-inhibition action (bacteriostatic action) on the bacteria in the culture medium as used in Example 1.

The antibacterial test for the aforementioned culture medium of Example 1 was carried out (where, as to the antibiotic agent concentration in the culture medium, the test is carried out after the following dilution series are prepared).

As to the antibacterial test, the bactericidal action and the bacteriostatic action on the bacteria were measured. The kind of the objective bacteria of the test was the following 6 bacteria in total: S. aureus IFO-12732, E. faecalis IFO-12970, and E. coli IFO-3301, which are aerobic bacteria; C. albicans IFO-1385 which is true fungus; and B. fragilis ATCC-25285 and P. anaerobius ATCC-27337, which are anaerobic bacteria. Hereinafter, a MIC measurement method of confirming the bacteriostatic action and a MBC measurement method of confirming the bactericidal action are explained.

(MIC Measurement Method):

As to the aerobic bacteria and the true fungus (the aforementioned four bacteria), the measurement was carried out according to procedures as defined in the National Committee for Clinical Laboratory Standards (NCCLS), except that: in the method for diluting liquid culture medium as defined in the Standards, the basal medium as mentioned in Example 1 was used as culture medium for measurement; the culture temperature and time are adjusted to 35° C. and 24 hours in the case of the aerobic bacteria, or adjusted to 25° C. and 72 hours in the case of the true fungus, the composition of the antibiotic agent (the kind of the antibiotic agent) was adjusted in the same way as of Example 1; and, as to the antibiotic agent concentration, the twice dilution series were prepared, in which the antibiotic agent concentration (penicillin: 1 mg/ml, kanamycin: 0.5 mg/ml, fungizone: 2.5 μg/ml, and vancomycin: 2 mg/ml) in the culture medium of Example 1 was regarded as a concentration of the original solution.

As to the anaerobic bacteria (the aforementioned two bacteria), the measurement was carried out according to procedures as defined in the standard method of the Chemotherapeutic Society of Japan, except that: in the method for diluting flat agar plate as defined in the Standards, agar culture medium (in a petri dish having a diameter of 9 cm) comprising the culture medium as mentioned in Example 1 was used as culture medium for measurement; the measurement environment was under an atmosphere of 5% $CO_2$, and the culture time was adjusted to 24 hours at 35° C.; the composition of the antibiotic agent was adjusted in the same way as of Example 1; and, as to the antibiotic agent concentration, the twice dilution series were prepared by regarding the antibiotic agent concentration of Example 1 as a concentration of the original solution. The anaerobic culture of the aforementioned condition was carried out in an anaerobic jar (Anaeropack KENKI, produced by Mitsubishi Gas Chemical Co., Ltd.).

As to the respective concentration stages (respective dilution series) of the antibiotic agent in both the aforementioned two MIC measurement methods, when the growth of bacteria was not observed with the naked eye after the culture, it was evaluated as (−). In reverse, when the growth of bacteria was observed, it was evaluated as (+). Their results were shown in Table 4. Of the concentration stages that were evaluated as (−), the minimum antibiotic agent concentration is defined as MIC (minimum inhibitory concentration).

(MBC Measurement Method):

As to the aerobic bacteria and the true fungus (the aforementioned four bacteria), one platinum loop with each of the culture mediums of all the concentration stages evaluated as (−) after the culture in the aforementioned MIC measurement methods are transplanted to Mueller-Hinton-Broth liquid culture medium which does not include an antibiotic agent each, but to which $Ca^{2+}Mg^{2+}$ is added (bouillon for measuring sensitivity, produced by Nissui Co., Ltd.), and are aerobically cultured under the same conditions of the culture temperature and time as the MIC measurement methods.

As to the anaerobic bacteria (the aforementioned two bacteria), an bactericidal absorbent cotton swab comes into contact with the agar culture medium of all the concentration stages evaluated as (−) after the culture in the aforementioned MIC measurement methods. Then, the agar culture medium is wiped out and transplanted to GAM agar culture medium not including an antibiotic agent each, and then the culture is anaerobically carried out under an atmosphere of 5% $CO_2$ and under the same conditions of the culture temperature and time as the MIC measurement methods.

As to the respective culture stages in both the aforementioned two MBC measurement methods, when the growth of bacteria was not observed with the naked eye after the culture, it was evaluated as (−). In reverse, when the growth of bacteria was observed, it was evaluated as (+). Their results were shown in Table 4. Of the stages that were evaluated as (−), the minimum oriented concentration (minimum antibiotic agent concentration when the MIC is measured) is defined as MBC (minimum bactericidal concentration).

ence as causes to decrease the cell proliferativity and success rate of the anticancer agent sensitivity test.

As to the test material and the number of cells as seeded (test material/number of cells as seeded), the following were used:

C-1 (human colon cancer cell line)/$1\times10^5$ cells/well

A-549 (human lung cancer cell line)/$1\times10^5$ cells/well

MKN-28 (human stomach cancer cell line)/$1\times10^5$ cells/well

HFL-1 and WI-38 (human fibroblast cells line)/$1\times10^5$ cells/well

Lung-k (human primary lung cancer cells)/$5\times10^5$ cells/well (in the preliminary culture step) or $2\times10^5$ cells/well (in the proliferative culture step)

The culture medium in the preliminary culture step was a culture medium as used in Example 1, and only the concentrations of the vancomycin (produced by Wako Pure Chemicals Co., Ltd.) therein were settled in the following conditions: 0.1 mg/ml, 0.5 mg/ml, 1.0 mg/ml, 1.5 mg/ml, 2.0 mg/ml, 2.5 mg/ml, 3.0 mg/ml, 4.0 mg/ml, and 5.0 mg/ml, and tests were carried out in each condition. In addition, a sample to which the vancomycin was not added was regarded as control.

As the culture medium in the proliferative culture step, one (for treatment of anticancer agents) obtained by adding the below-mentioned anticancer agents to the culture medium as used in Example 1 was used. In addition, the

TABLE 4

| Antibiotic agent twice dilution series (dilution) | | $2^1$ times | $2^2$ times | $2^3$ times | $2^4$ times | $2^5$ times | $2^6$ times | $2^7$ times | $2^8$ times | $2^9$ times | $2^{10}$ times | $2^{11}$ times | $2^{12}$ times | $2^{13}$ times |
|---|---|---|---|---|---|---|---|---|---|---|---|---|---|---|
| S. aureus | MIC | (−) | (−) | (−) | (−) | (−) | (−) | (−) | (−) | (−) | (−) | (−) | (+) | (+) |
| IFO-12732 | MBC | (−) | (−) | (−) | (−) | (−) | (−) | (−) | (−) | (−) | (−) | (+) | (+) | (+) |
| E. faecalis | MIC | (−) | (−) | (−) | (−) | (−) | (−) | (−) | (−) | (−) | (+) | (+) | (+) | (+) |
| IFO-12970 | MBC | (−) | (−) | (−) | (−) | (−) | (+) | (+) | (+) | (+) | (+) | (+) | (+) | (+) |
| E. coli | MIC | (−) | (−) | (−) | (−) | (−) | (−) | (+) | (+) | (+) | (+) | (+) | (+) | (+) |
| IFO-3301 | MBC | (−) | (−) | (−) | (−) | (−) | (+) | (+) | (+) | (+) | (+) | (+) | (+) | (+) |
| C. albicans | MIC | (−) | (−) | (−) | (−) | (+) | (+) | (+) | (+) | (+) | (+) | (+) | (+) | (+) |
| IFO-1385 | MBC | (−) | (−) | (−) | (+) | (+) | (+) | (+) | (+) | (+) | (+) | (+) | (+) | (+) |
| B. fragilis | MIC | (−) | (−) | (−) | (−) | (−) | (−) | (+) | (+) | (+) | (+) | (+) | (+) | (+) |
| ATCC-25285 | MBC | (−) | (−) | (−) | (−) | (−) | (+) | (+) | (+) | (+) | (+) | (+) | (+) | (+) |
| P. anaerobius | MIC | (−) | (−) | (−) | (−) | (−) | (−) | (−) | (−) | (−) | (−) | (−) | (−) | (−) |
| ATCC-27337 | MBC | (−) | (−) | (−) | (−) | (−) | (−) | (−) | (−) | (−) | (−) | (−) | (+) | (+) |

(Result and Consideration):

The culture medium as used in Example 1 displays a sufficient killing action and multiplication-inhibition action on all kinds of the aforementioned objective bacteria, and these actions can be maintained until the end of the culture even if the decrease of the potency may be expected due to such as overlong culture.

<<Confirmation Test of Cell Toxicity According to Vancomycin Amount>>

The antibiotic agent in the culture medium as used in Example 1 included vancomycin, but it was additionally confirmed whether the vancomycin has a unfavorable influence upon characters of the aimed cells according to the vancomycin amount or not.

Specifically, it is confirmed whether the vancomycin in the culture medium of the preliminary culture step has a unfavorable influence upon the cell proliferativity in the preliminary culture step, the cell proliferativity in the proliferative culture step, and the anticancer agent sensitivity test results or not, and then the following test was carried out. Herein, the unfavorable influence means such an influculture medium including no anticancer agent as used in Example 1 was used as control (for non-treatment of anticancer agents).

Taxol (0.05 μl/ml)

Taxotere (0.1 μl/ml)

Gemcitabine (1.0 μl/ml)

Navelbine 0.05 μl/ml)

(Test Method in Preliminary Culture Step):

A culture supporting base was prepared by coating a 6-well multiplate (well surface area (basal surface area): 9.6 $cm^2$) with collagen gel to form its layer. As to the five cell lines and one primary cell, their seeding was carried out with the aforementioned number of cells as seeded, and the cells were overlaid with 5 ml of the culture medium. Thereafter, the monolayer culture was carried out for 48 hours.

Figure 2:
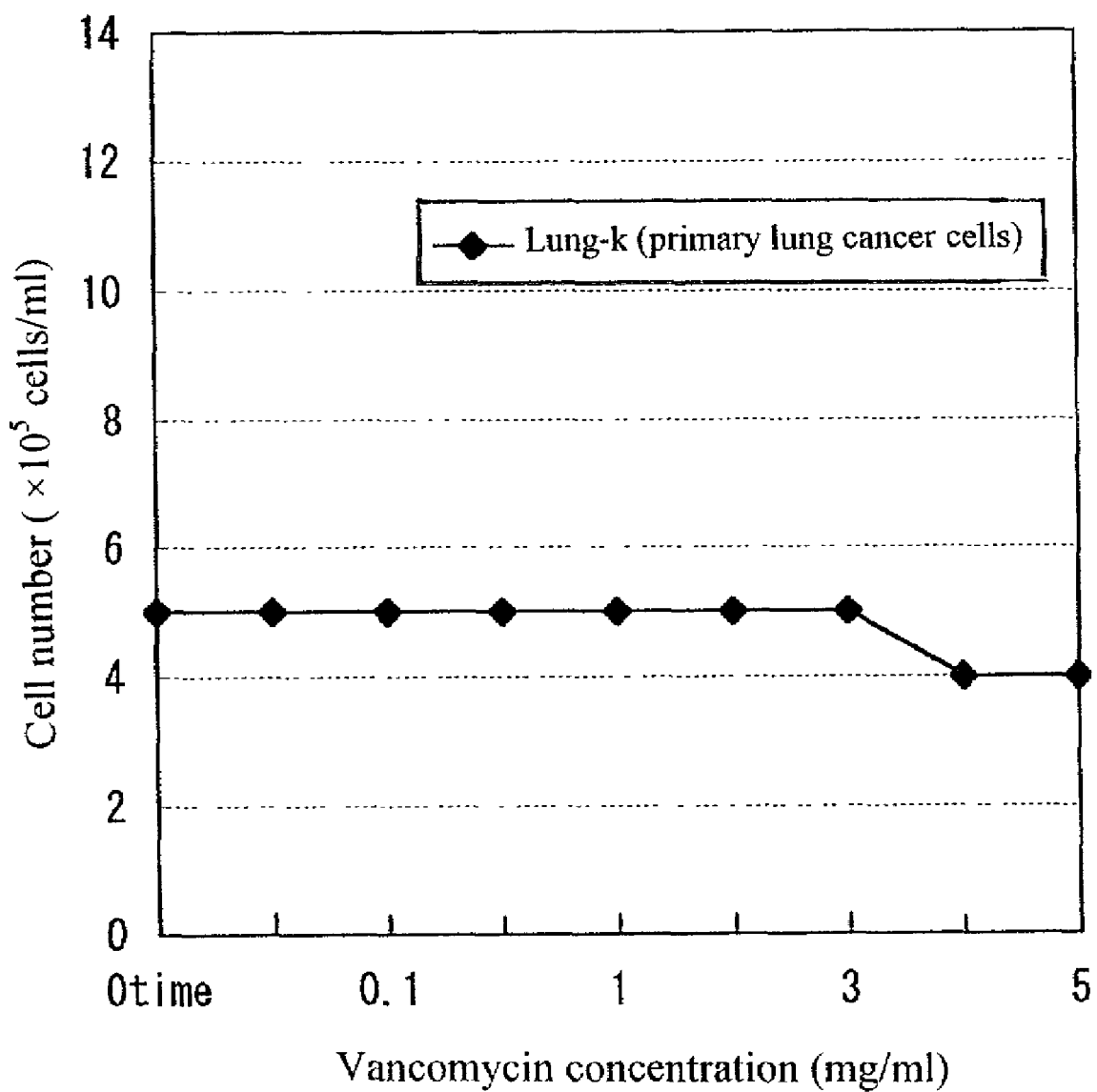
FIG. 2 is a graph representing an influence of the vancomycin concentration in the preliminary culture step upon the cell proliferativity in the preliminary culture step (concerning primary lung cancer cells).

After 24 hours from the beginning of the culture, the resultant live cells as adhered to the supporting base were collected. After the cells were counted with a blood-cell counter board, the cell number per 1 mil of the culture medium was calculated, and the cell proliferativity in the preliminary culture step was observed. Their results were shown in FIGS. 1 and 2.

(Test Method in Proliferative Culture Step):

The cells were collected from only the cells having a concentration condition in which the cell proliferativity was good in the preliminary culture step, and the proliferative culture step was carried out by way of the cells-seeding step and embedding step according to the specific procedures the (1) to (3) below. Thereafter, the evaluation of the cell proliferativity and anticancer agent sensitivity test were carried out.

(1) The above five cell lines and one primary cell are mixed to a collagen solution so as to adjust to the aforementioned cells-seeding number, and then droplets (n=6) of 30 μl/droplet are prepared on a 6-well test plate.

(2) After the droplets were gelled, the resultant droplets were overlaid with the culture medium including the above various anticancer agents, and thereafter the culture is carried out for 7 days. Incidentally, the culture is carried out at 37° C. in a 5% $CO_2$ incubator.

(3) After 24 hours from the beginning of the culture, a dish (0 time) is stained and fixed.

(4) After 7 days from the beginning of the culture, the NR stain is carried out, and the cells are fixed by neutral buffered formalin to complete the culture.

Figure 3:
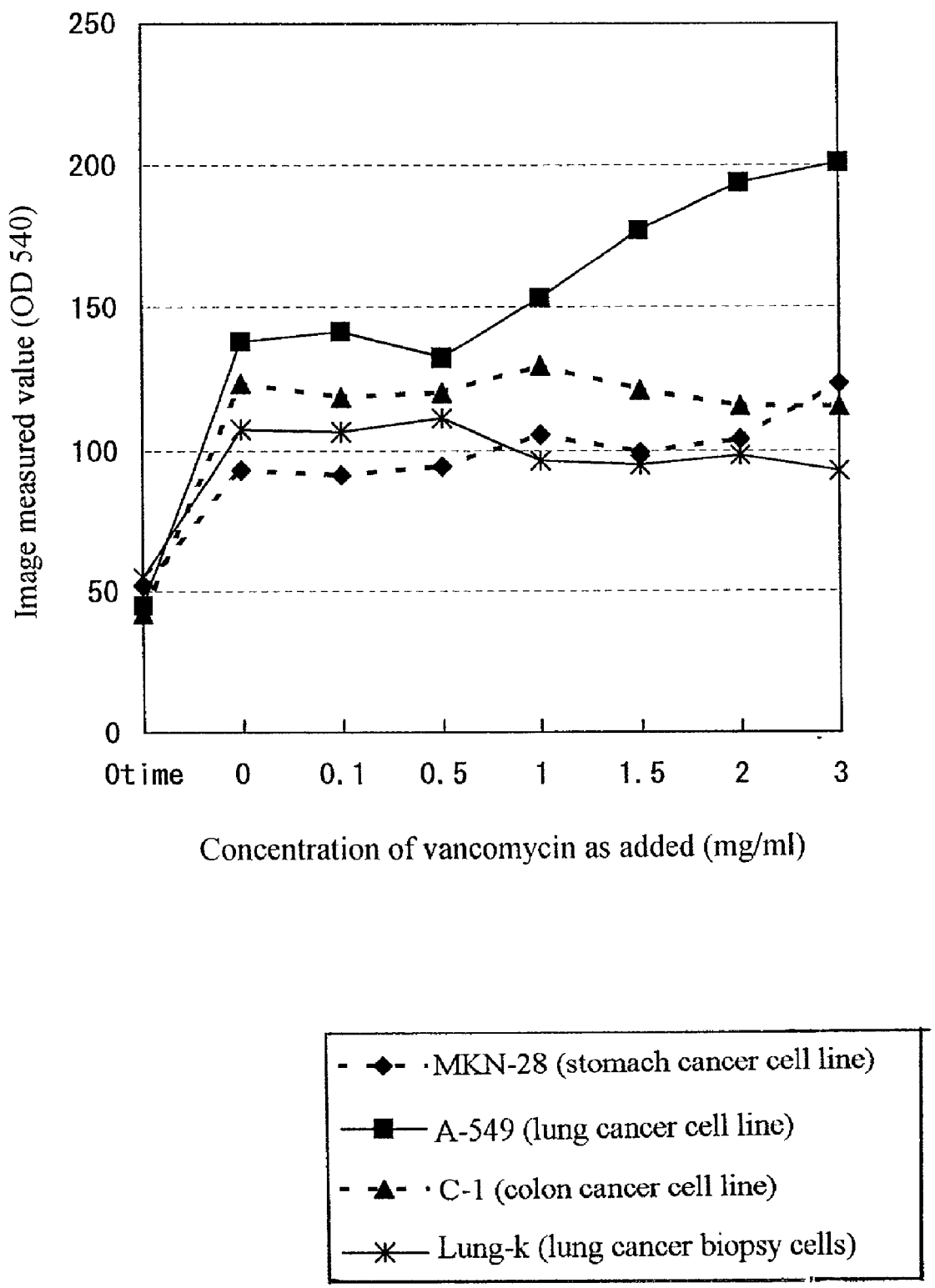
FIG. 3 is a graph representing an influence of the vancomycin concentration in the preliminary culture step upon the cell proliferativity in the proliferative culture step (concerning a cancer cell line and primary lung cancer cell).
Figure 4:
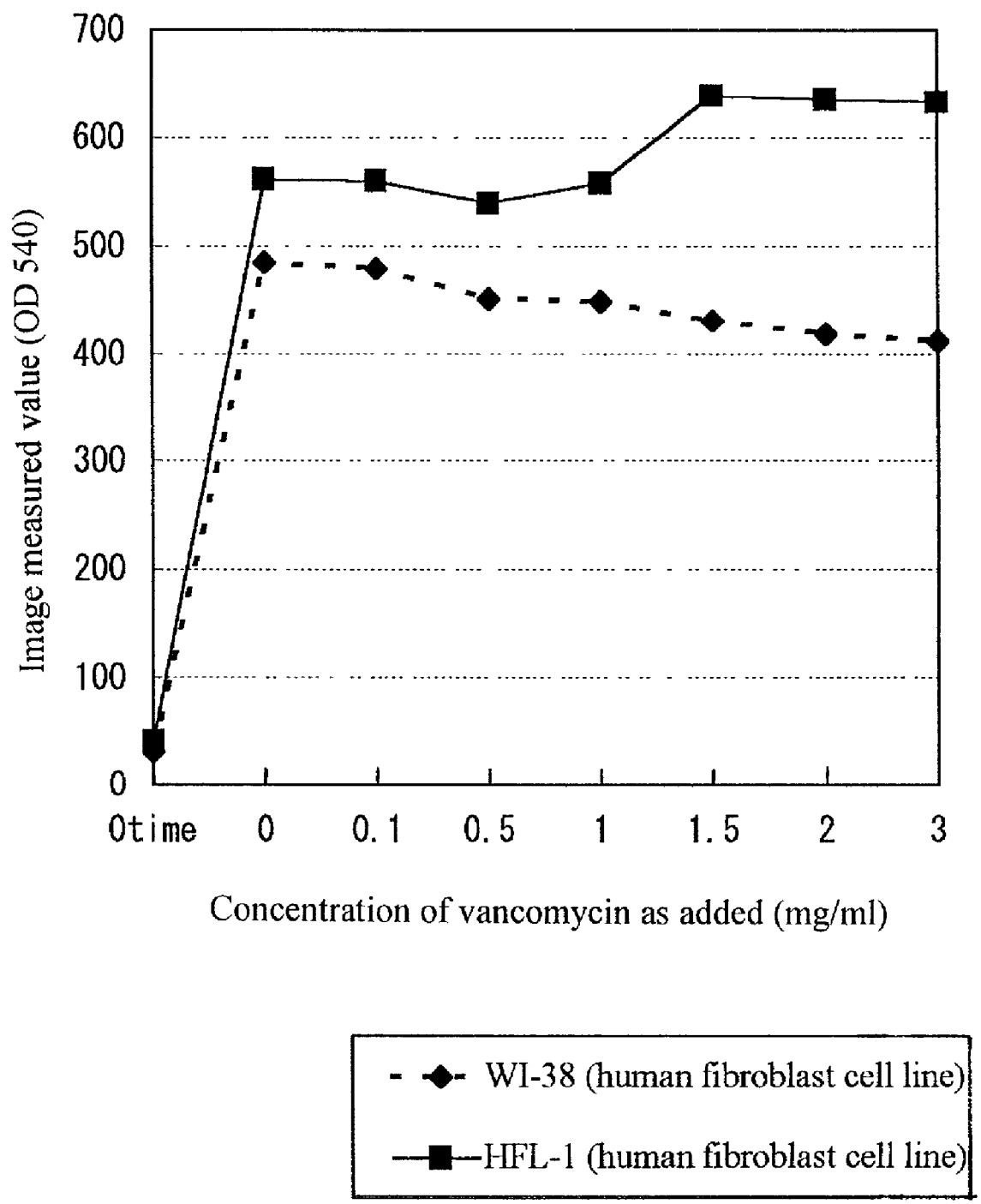
FIG. 4 is a graph representing an influence of the vancomycin concentration in the preliminary culture upon step the cell proliferativity in the proliferative culture step (concerning a fibroblast cell line).
Figure 5:
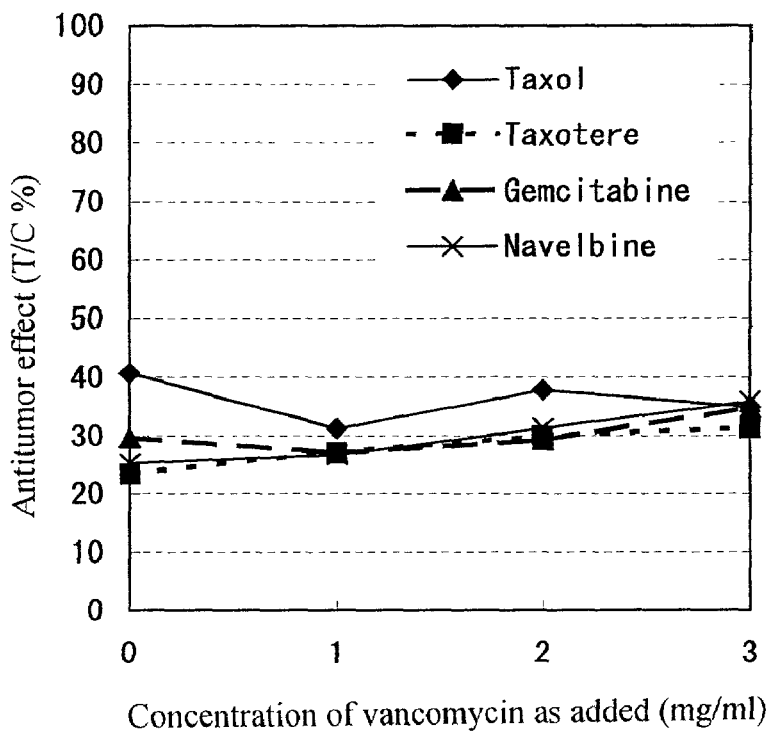
FIG. 5 is a graph representing an influence of the vancomycin concentration in the preliminary culture step upon the anticancer agent sensitivity test results (concerning a human lung cancer cell line A-549).
Figure 6:
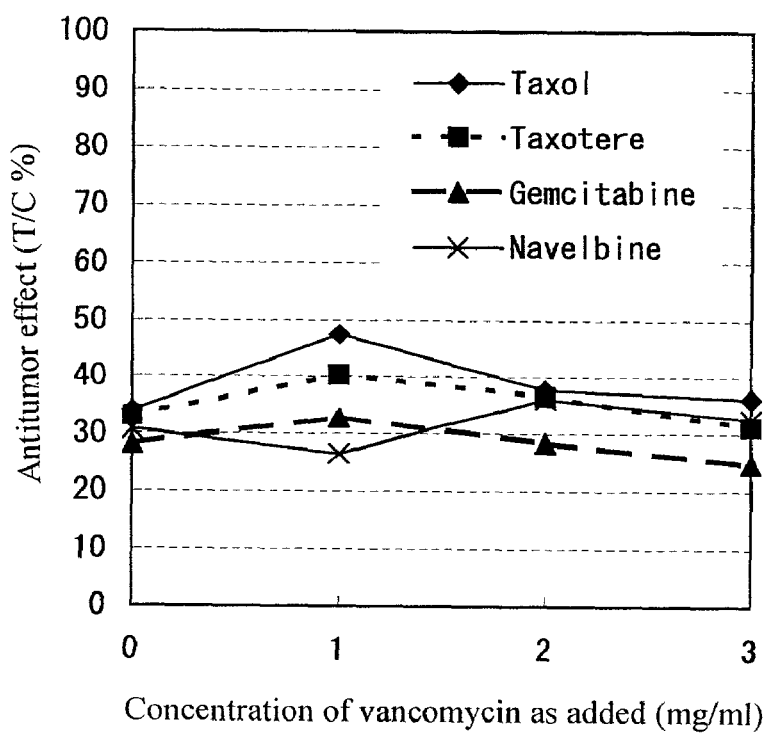
FIG. 6 is a graph representing an influence of the vancomycin concentration in the preliminary culture step upon the anticancer agent sensitivity test results (concerning a human gastric cancer cell line MKN-28).
Figure 7:
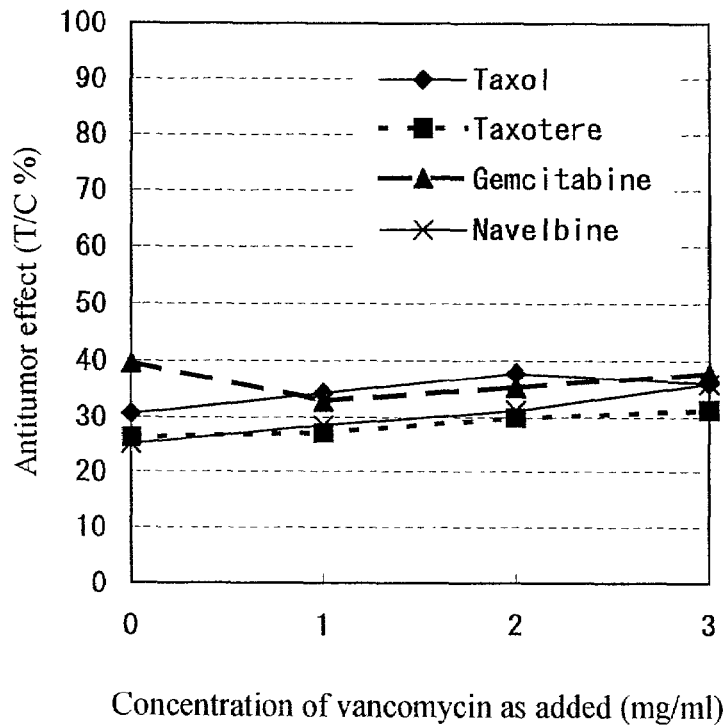
FIG. 7 is a graph representing an influence of the vancomycin concentration in the preliminary culture step upon the anticancer agent sensitivity test results (concerning a human colon cancer cell line C-1).
Figure 8:
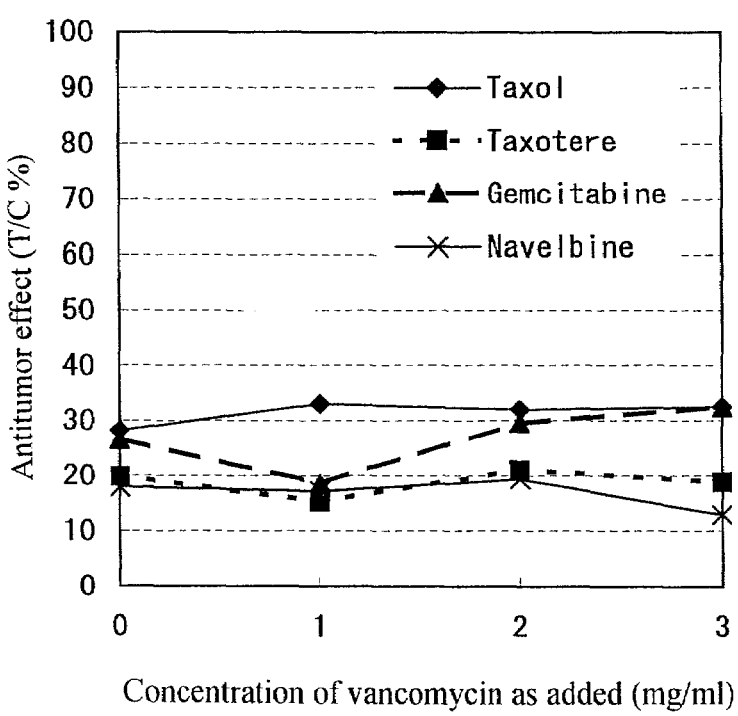
FIG. 8 is a graph representing an influence of the vancomycin concentration in the preliminary culture step upon the anticancer agent sensitivity test results (concerning a human fibroblast cell line HFL-1).
Figure 9:
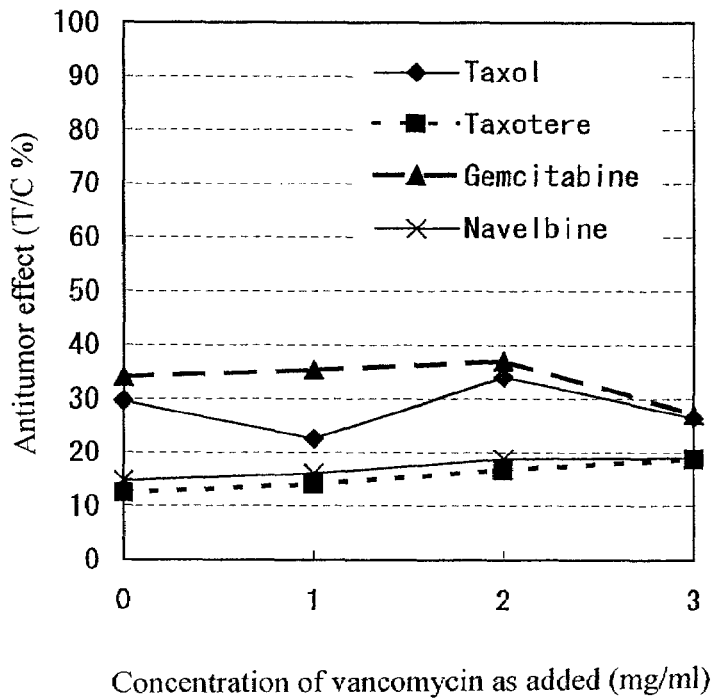
FIG. 9 is a graph representing an influence of the vancomycin concentration in the preliminary culture step upon the anticancer agent sensitivity test results (concerning a human fibroblast cell line WI-38).
Figure 10:
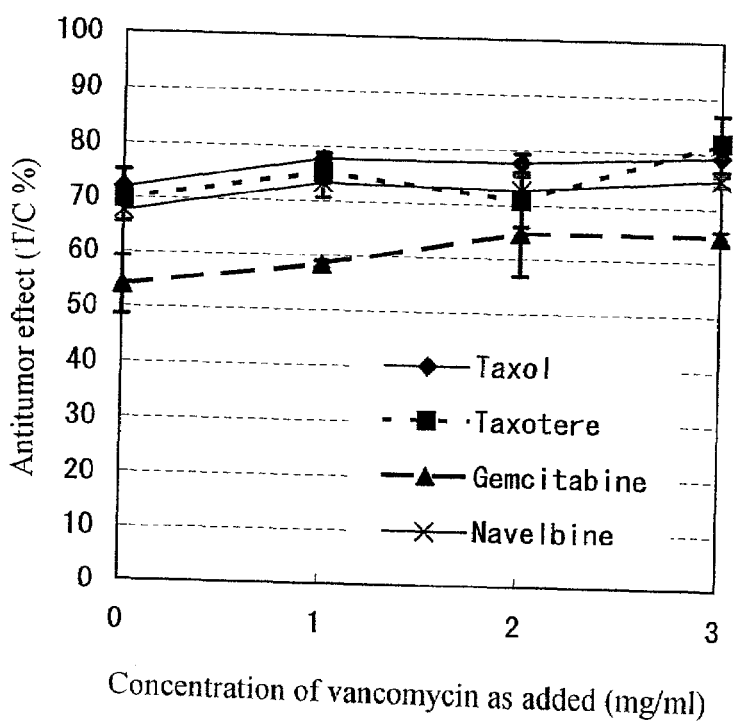
FIG. 10 is a graph representing an influence of the vancomycin concentration in the preliminary culture step upon the anticancer agent sensitivity test results (concerning human primary lung cancer cells Lung-k).

(5) The resultant test plate is quantitatively analyzed with an image analyzer, and then the unfavorable influence upon the cell proliferativity and the anticancer agent sensitivity test results (antitumor effect T/C (%): relative proliferation ratio T/C (%) between a group non-treated with anticancer agents (C) and a group treated with anticancer agents (T), in the case where the ratio is not more than 50%, it is defined as having a sensitivity.) are observed. Incidentally, the evaluation of the cell proliferativity is carried out on the basis of the value at 0 time. The results of the cell proliferativity in the proliferative culture step were shown in FIGS. 3 and 4, and the results of the anticancer agent sensitivity test were shown in FIGS. 5 to 10.

(Results and Consideration):

As to the unfavorable influence upon the cell proliferativity in proportion to the amount of the vancomycin as added in the preliminary culture step, when the vancomycin was not added, the good cell proliferation was observed in the various cells after 48 hours from the beginning of the culture. When the vancomycin was added, the cell proliferation in a condition of its concentration of not more than 2.0 mg/ml was as good as that in a condition such that the vancomycin was not added. On the other hand, when the vancomycin was not added or the vancomycin concentration was at least not more than 3.0 mg/ml, the cell number when the cells-seeding step was carried out could be maintained in the human primary culturing cells after 48 hours from the beginning of the culture, and the cell toxicity (cells-killing action) of the culture medium was not observed.

As to the unfavorable influence upon such as the cell proliferativity in the proliferative culture step, used were the cells having good cell proliferativity after the preliminary culture step, namely the cells that were cultured in a condition such that the amount of the vancomycin as added was not more than 3.0 mg/ml. It was understood that these all have good cell proliferativity after the 7 days from the culture, and the unfavorable influence upon the cell proliferativity in the proliferative culture step is not found depending upon the amount of the vancomycin as added in the preliminary culture step. In addition, it was understood that there is no unfavorable influence upon the anticancer agent sensitivity test results (antitumor effect T/C (%)) depending upon the amount of the vancomycin as added in the preliminary culture step.

In addition, it is said that: according to the above additional confirmation (the confirmation of the unfavorable influence caused by the amount of the vancomycin as added), the proliferating action that the culture medium had was displayed from the good cell proliferativity; in addition, the physiological activity-retaining action that the culture medium had was displayed from the anticancer agent sensitivity test results.

COMPARATIVE EXAMPLE 1

The anticancer agent sensitivity test was carried out in the same way as of Example 1 except that: the culture medium as used was adjusted to the composition shown below; and the washing step was added between the step (1) and the step (2) as shown in the aforementioned flow sheet of Table 1; and a culture flask having a surface area of 25 $cm^2$ was used as the supporting base in the preliminary culture step. Then, the results were evaluated. Incidentally, breast cancer cells, lung cancer cells, and colon cancer cells were used as the cells subjected to the test in Comparative Example 1. The results were shown in Tables 2 and 3.

As to the culture medium as optionally used in each step in Comparative Example 1, used was a culture medium as prepared by adding penicillin and kanamycin to the following basal medium.

Basal Medium:

DF culture medium (DF: a mixed culture medium containing one volume of Dulbecco modified Eagle (DME) culture medium and one volume of Hams F12 culture medium)+10% FBS (FBS: fetal bovine serum)+5 μg/ml insulin (product of Sigma Co.)+10 ng/ml EGF (product of Collaborative Co.; EGF (epidermal growth factor))

Penicillin, Kanamycin:

One 1 g-vial of penicillin (product of Toyama Chemical Co., Ltd.; for penicillin injection) and 1 g potency of kanamycin (product of GIBCO BRL Co., Ltd.; sulfuric acid kanamycin reagent) are dissolved into 20 ml of PBS, and the resultant solution is added to the basal medium in such an amount as gives a concentration of 0.2% (final concentration of penicillin and kanamycin=0.1 mg/ml each) on the basis of the basal medium.

[Washing Step]:

Five sterilization-treated plastic dishes having diameters of 10 cm were prepared, and about 25 ml of physiological saline for injection is added to each dish. After biopsy materials as the test materials were sampled, they are picked out with a sterilized pincette and washed by moving them in the physiological saline in the first dish a few times. After the washing in the first dish, the same procedure is also carried out for the second to fifth dishes. Thereafter, the biopsy materials are moved in a culture medium as used in the above Comparative Example 1 to wash them, and then supplied to the separating and/or dispersing treatments.

Incidentally, the antibacterial test was carried out in the same way as of Example 1 so as to confirm the killing action (bactericidal action) and the multiplication-inhibition action (bacteriostatic action) on the bacteria in the culture medium as used in Comparative Example 1.

However, the kind of the objective bacteria of the test was the following 4 bacteria in total: *S. aureus* IFO-12732, *E.* faecalis IFO-12970, and E. coli IFO-3301, which are aerobic bacteria; and C. albicans IFO-1385 which is true fungus, and the culture medium (comprising 0.1 mg/ml of penicillin and 0.11 mg/ml of kanamycin as the antibiotic agent) was the same as of Comparative Example 1. As to the antibiotic agent concentration, the twice dilution series were prepared, in which the antibiotic agent concentration in the culture medium of Comparative Example 1 was regarded as a concentration of the original solution. Then, the MIC measurement and MBC measurement were carried out in the same way as of Example 1. The results were shown in Table 5.

TABLE 5

| Anitbiotic agent twice dilution series (dilution) | | $2^1$ times | $2^2$ times | $2^3$ times | $2^4$ times | $2^5$ times | $2^6$ times | $2^7$ times | $2^8$ times | $2^9$ times | $2^{10}$ times | $2^{11}$ times | $2^{12}$ times | $2^{13}$ times |
|---|---|---|---|---|---|---|---|---|---|---|---|---|---|---|
| S. aureus | MIC | (−) | (−) | (−) | (+) | (+) | (+) | (+) | (+) | (+) | (+) | (+) | (+) | (+) |
| IFO-12732 | MBC | (−) | (+) | (+) | (+) | (+) | (+) | (+) | (+) | (+) | (+) | (+) | (+) | (+) |
| E. faecalis | MIC | (−) | (+) | (+) | (+) | (+) | (+) | (+) | (+) | (+) | (+) | (+) | (+) | (+) |
| IFO-12970 | MBC | (+) | (+) | (+) | (+) | (+) | (+) | (+) | (+) | (+) | (+) | (+) | (+) | (+) |
| E. coli | MIC | (−) | (−) | (+) | (+) | (+) | (+) | (+) | (+) | (+) | (+) | (+) | (+) | (+) |
| IFO-3301 | MBC | (+) | (+) | (+) | (+) | (+) | (+) | (+) | (+) | (+) | (+) | (+) | (+) | (+) |
| C. albicans | MIC | (+) | (+) | (+) | (+) | (+) | (+) | (+) | (+) | (+) | (+) | (+) | (+) | (+) |
| IFO-1385 | MBC | (+) | (+) | (+) | (+) | (+) | (+) | (+) | (+) | (+) | (+) | (+) | (+) | (+) |

EXAMPLE 2

<<Selection of Culture Supporting Base Area>>

As to the culture supporting base as used in the culturing process according to the present invention, especially the culture supporting base usable in the preliminary culture step, the selection of the surface area (when a container having the supporting base is a dish, the surface area means a basal area.) was confirmed by experiment.

As the test materials, human primary cells (lung cancer cells) were used. As to containers having the culture supporting base, 6-well, 12-well, 24-well, and 48-well multiplates were used. The surface areas (base areas) of the wells that each plate has are 9.6 cm$^2$, 3.8 cm$^2$, 2.0 cm$^2$, and 0.8 cm$^2$ respectively in order. The base surfaces of these four dishes were coated with a Type-I collagen gel to form a basal layer, thus completing the culture supporting base.

In each dish, the cells having a cell number of 1×10$^5$ to 1×10$^4$ cells/well (specifically, 4 patterns of 1×10$^5$, 5×10$^4$, 2×10$^4$, and 1×10$^4$ cells/well) were seeded, and they were cultured at 37° C. in a 5% CO$_2$ incubator. As to the culture medium, the culture medium as used in Example 1 was used.

After 24 hours from the beginning of the culture, the culture medium was exchanged, and only the cells as fixed to the collagen gel were collected. In addition, the values of the number of the live cells after 24 hours and 72 hours from the beginning of the culture were evaluated by colorimetric quantitative method. Then, the initial adhesion (OD$_{540}$) of the culture cells based on the surface area (base area) of the culture supporting base and the cell proliferativity ratio after 72 hours from the beginning of the culture were calculated. The results of the initial adhesion and the results of the cell proliferativity ratio were shown in FIGS. 11 and 12 respectively.

Incidentally, the above cell proliferativity ratio is defined as a ratio of the OD$_{540}$ after 72 hours from the beginning of the culture based on the OD$_{540}$ after 24 hours from the beginning of the culture.

(Colorimetric Quantitative Method):

A MTT reagent (produced by Sigma Co.) was dissolved in a PBS so that the concentration would be 5 mg/ml, and it was added to DF culture medium so that the concentration would be 10%. A definite amount of this reagent came into contact with the cells after the culture, and then was allowed to react for 3 to 4 hours. After the end of the reaction, the reagent was removed, and a definite amount of DMSO (dimethylsulfoxide) was added thereto, and then the resultant precipitated formazan crystal was dissolved. (The resultant solution was colored blue.) The reaction liquid as obtained in this way was divided in a definite amount and put in a 96-well multiplate. Then, the colorimetric quantification was carried out with a microplate reader (using a filter of 540 nm), and then the OD of the live cells was measured.

Figure 11:
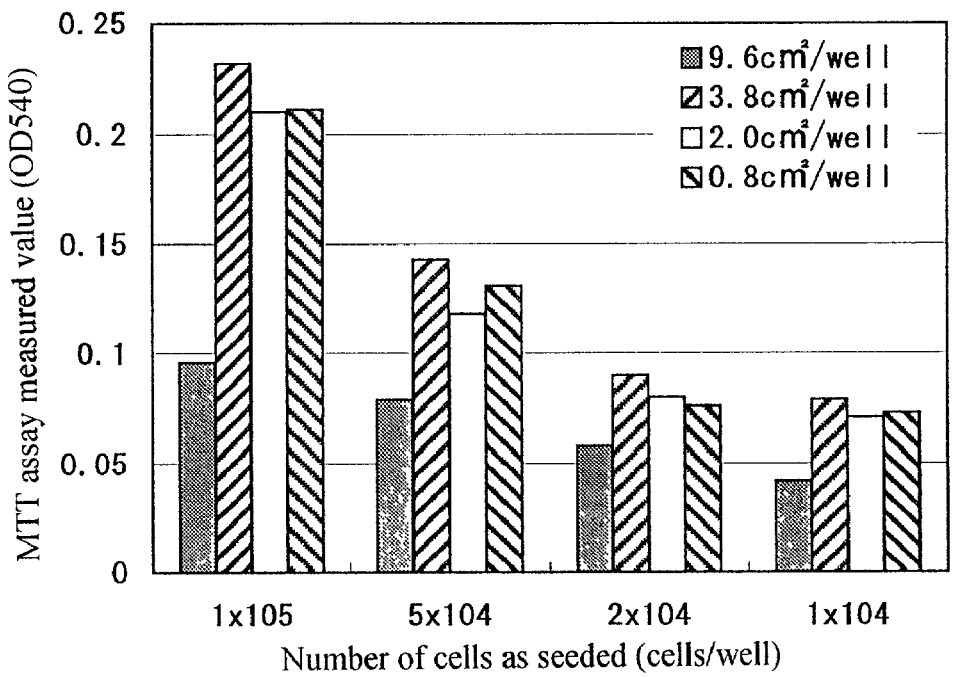
FIG. 11 is a graph representing an influence of the surface area of the supporting base, as used in the preliminary culture step, upon the initial adhesion of the tumor cells.
Figure 12:
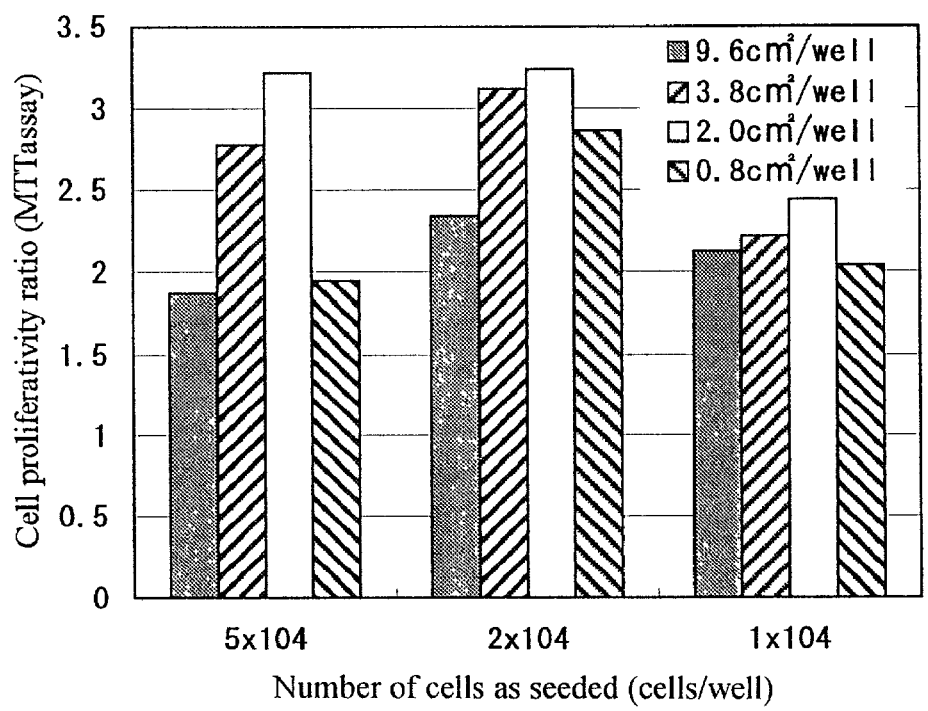
FIG. 12 is a graph representing an influence of the surface area of the supporting base, as used in the preliminary culture step, upon the cell proliferativity ratio of the tumor cells.

(Results and Consideration):

From graphs as shown in FIGS. 11 and 12, it was understood that: when the supporting bases have surface areas (base areas) of 2.0 cm$^2$ and 3.8 cm$^2$, the supporting bases have the most excellent initial adhesion and a high cell proliferativity ratio.

EXAMPLE 3

<<Selection of Culture Supporting Base Shape>>

As to the culture supporting base as used in the culturing process according to the present invention, especially the culture supporting base usable in the preliminary culture step, the selection of the container shape of the supporting base and its effect were confirmed by experiment.

As the test materials, namely the biopsy cells, human primary cells (lung cancer cells and breast cancer cells) as obtained by sampling for biopsy or by surgically resection were used. As to a container with the culture supporting base, the tube container as shown in FIGS. 13 and 14 (the cutting face (flat face) is a portion where the cells adhere and the culture is carried out, and the surface area of this portion is 5.5 cm$^2$) and a culture flask having a surface area of 5.5 cm$^2$ were used. Both containers are plastic containers. The collagen gel coating was formed by overlaying the base of these two culture containers with a 0.3% Type-I collagen solution (the same 0.3% Type-I neutralized collagen solution as used in the embedding step of Example 1) with a thickness of 1 mm and gelling at 37° C., thus completing the culture supporting base.

After the above human primary cells (lung cancer cells and breast cancer cells) were enzymatically dispersed for 1 to 2 hours, the unnecessary tissue was removed by a nylon mesh having a pore size of 300 μm, and the size of the cell clump was adjusted. Next, the cell number was counted with a hematocytometer, and a dispersion including $1 \times 10^5$ cells was prepared. Thereafter, the cells were seeded on the above various culture supporting bases in two patters of $5 \times 10^4$ cells and $1 \times 10^5$ cells, and then they were cultured (preliminarily cultured) in a 5% $CO_2$ incubator of 37° C. In detail, in the above tube container and flask container each, 12 samples having a cell number of $1 \times 10^5$ cells and 8 samples having a cell number of $5 \times 10^4$ cells of the lung cancer cells were seeded, and 4 samples having a cell number of $1 \times 10^5$ cells and 1 sample having a cell number of $5 \times 10^4$ cells of the breast cancer cells were seeded, and then they were cultured. Incidentally, as to the culture medium, the culture medium as used in Example 1 was used, and then it was overlaid with 10 ml of the culture medium each.

After 48 hours from the beginning of the culture, the culture medium was exchanged, and such as blood cell components and dead cells suspended in the culture medium were removed, and the collagen gel layer was dissolved by a 0.1% collagenase solution, and then only the cells as fixed to the collagen gel were collected.

The cells as collected from each supporting base were suspended in 0.5 ml of a 0.3% Type-I collagen solution (the same 0.3% Type-I neutralized collagen solution as used in the embedding step of Example 1), and then a globular collagen gel (collagen gel droplet) of 30 μl was produced. Incidentally, 9 droplets were produced per sample, and the following analysis and measurement were carried out, and then their average values were defined as their results. After the above collagen gel droplets were produced, the bioassay (calorimetric analysis) was immediately carried out by a Neutral Red staining liquid. Thereby, the image absorbency value is measured and the live cell number was converted from this absorbency. The graphs describing the results of measuring and calculating the above absorbency ($OD_{540}$) and live cell number are shown in FIGS. 15, 16, 17, and 18.

Figure 15:
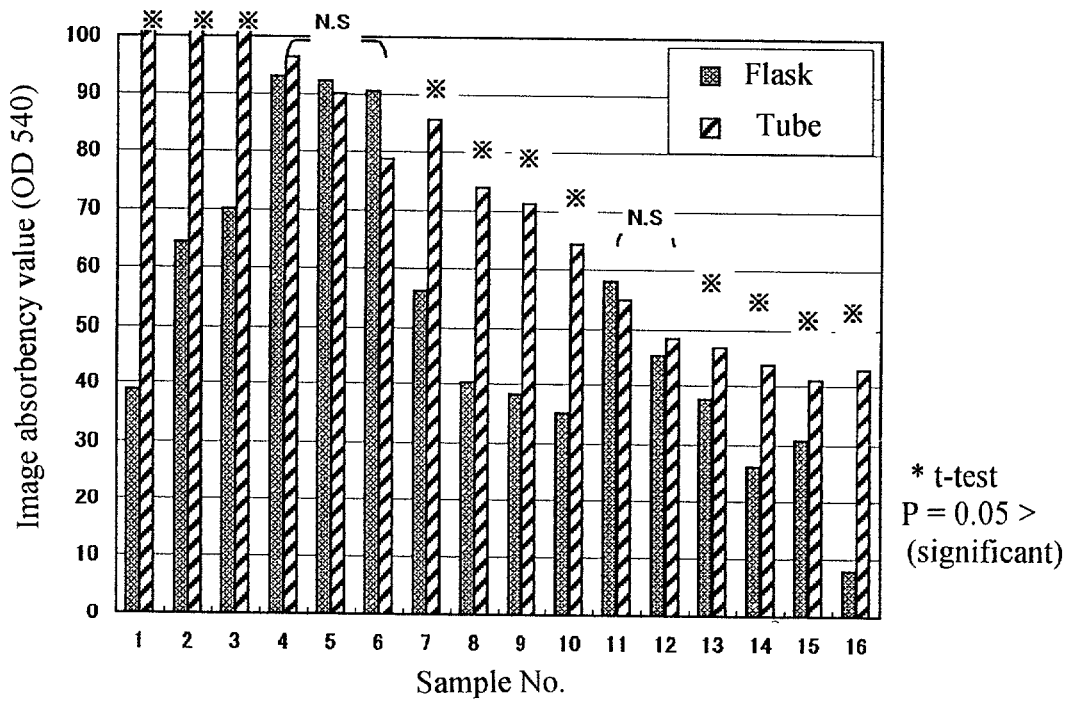
FIG. 15 is a graph concerning the effect (in terms of $OD_{540}$) of the shape of the supporting base, as used in the preliminary culture step, upon collection of living cells of tumor cells.
Figure 16:
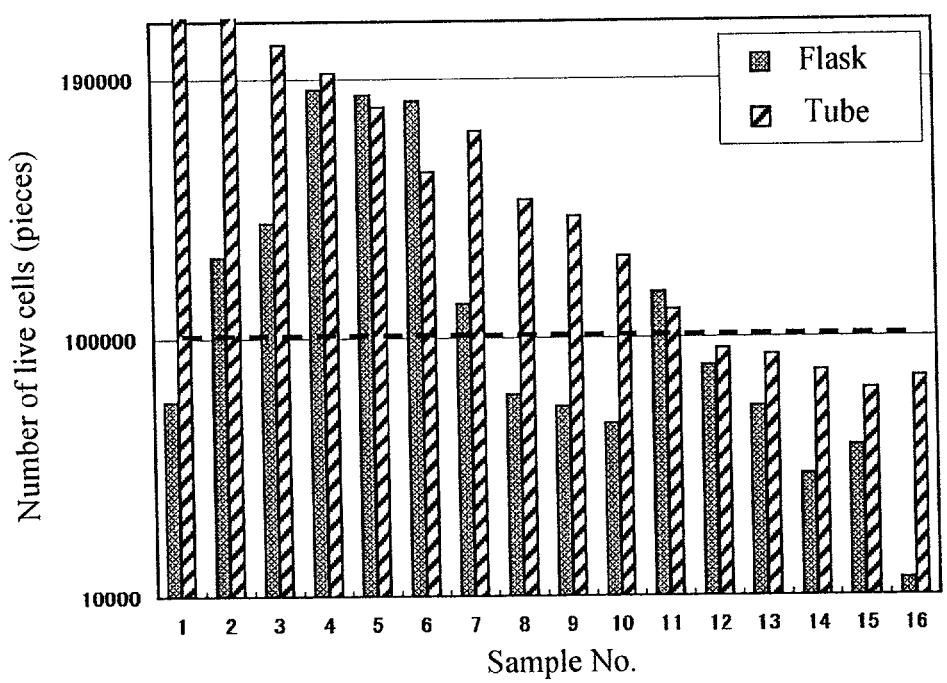
FIG. 16 is a graph concerning the effect (in terms of the number of living cells) of the shape of the supporting base, as used in the preliminary culture step, upon collection living cells of tumor cells.
Figure 17:
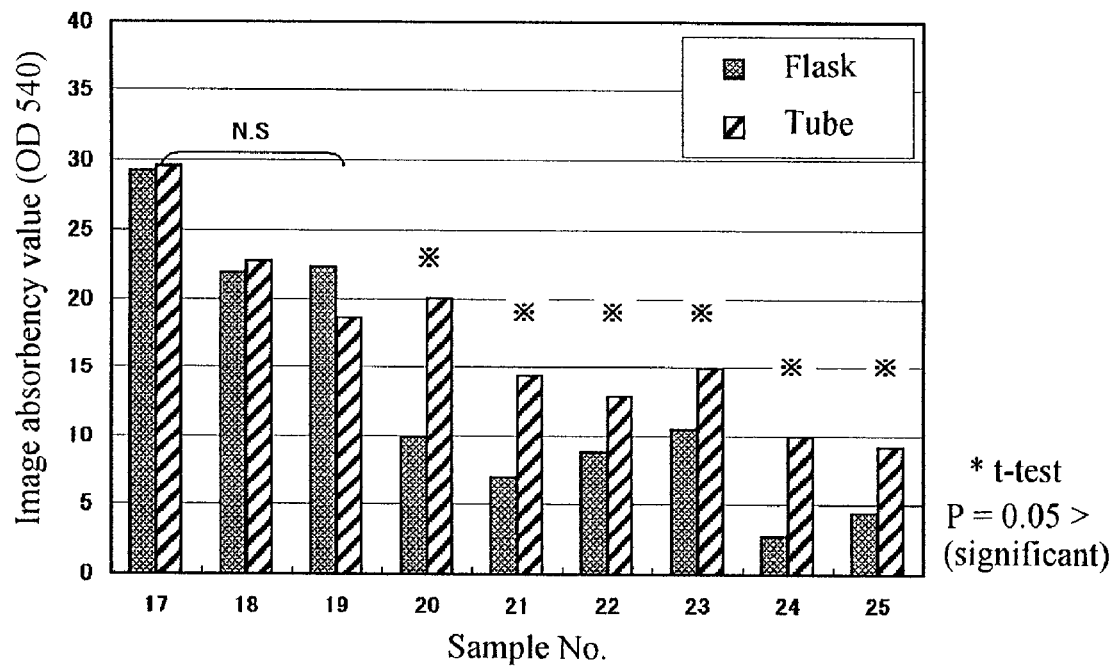
FIG. 17 is a graph concerning the effect (in terms of $OD_{540}$) of the shape of the supporting base, as used in the preliminary culture step, upon collection of living cells of tumor cells.
Figure 18:
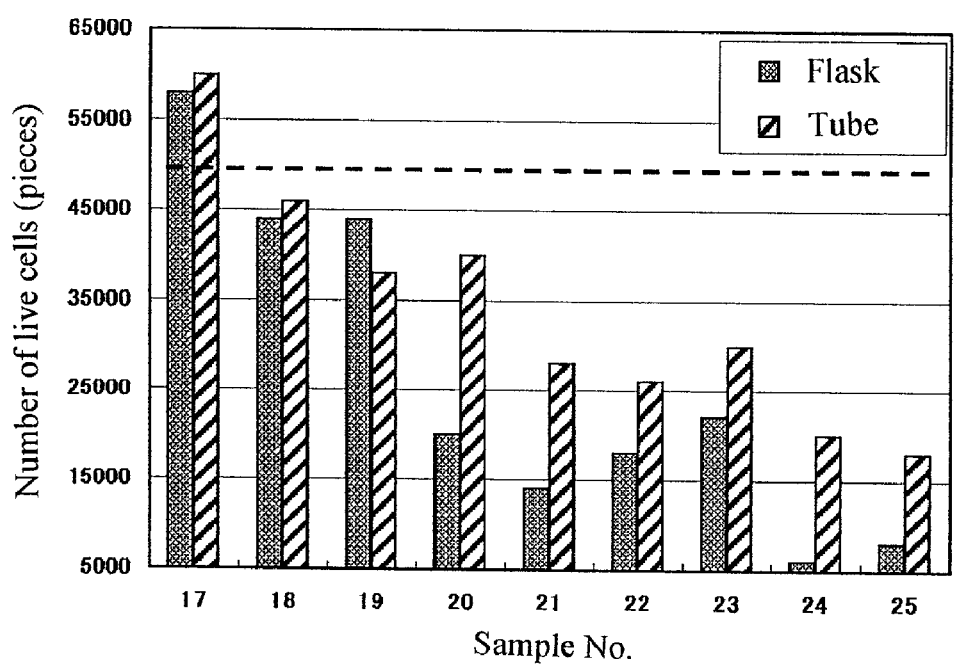
FIG. 18 is a graph concerning the effect (in terms of the number of living cells) of the shape of the supporting base, as used in the preliminary culture step, upon collection living cells of tumor cells.

Incidentally, FIG. 15 relates to the absorbency of the sample obtained by seeding in a cell number of $1 \times 10^5$ cells, FIG. 16 relates to the live cell number of the sample obtained by seeding in a cell number of $1 \times 10^5$ cells, FIG. 17 relates to the absorbency of the sample obtained by seeding in a cell number of $5 \times 10^4$ cells, and FIG. 18 relates to the live cell number of the sample obtained by seeding in a cell number of $5 \times 10^4$ cells. In addition, as to the sample number in the figures, No. 4, 6, 12, 13, and 23 relate to breast cancer cell samples, and the others relate to lung cancer cell samples. The broken line in FIGS. 16 and 18 represents the number of the live cells as seeded.

In addition, for the purpose of evaluating the maintenance of cell life after the preliminary culture, the collagen gel droplet in which the cells after the preliminary culture was embedded was prepared as mentioned above, and the embedded culture of the collagen gel droplet was carried out for 7 days. Thereby, the cell proliferativity ratio for the 7 days' embedded culture was calculated, and the cell proliferativity of all the cell samples that were preliminarily cultured in the above tube and flask was confirmed. Specifically, for each sample, the cells collected from the individual supporting bases were suspended in a 0.3% Type-I collagen solution (the same 0.3% Type-I neutralized collagen solution as used in the embedding step of Example 1) so that the concentration would be $1 \times 10^5$ cells/ml, and 6 globular collagen gels (collagen gel droplets) of 30 Pl were produced per sample. As to the three droplets of these, the bio-assay (calorimetric analysis) by a Neutral Red staining liquid was immediately carried out after the droplets were prepared, and the image absorbencies were measured, and then the average value was calculated. As to the residual three droplets, the colorimetric analysis was carried out in the same way as shown above, and the average is calculated after the serum-free culture was carried out for 7 days. The cell proliferativity ratio of each sample was calculated as a ratio of the image absorbency value after 7 days' embedded culture based on the image absorbency value before the culture.

Figure 19:
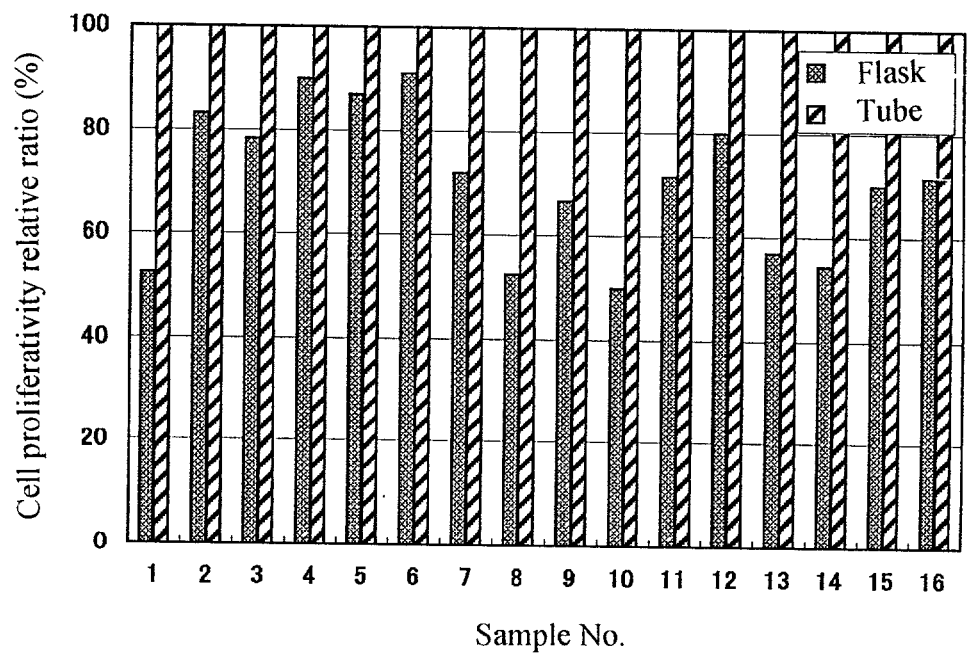
FIG. 19 is a graph representing the cell proliferativity ratio of cells during the embedding culture wherein the cells are derived from culture on each supporting base.
Figure 20:
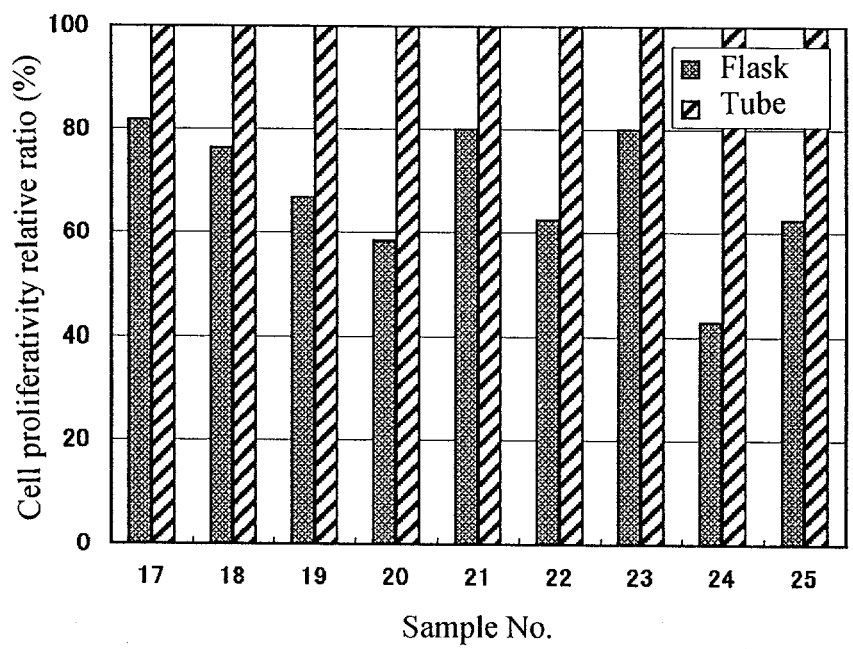
FIG. 20 is a graph representing the cell proliferativity ratio of cells during the embedding culture wherein the cells are derived from culture on each supporting base.

As to the cell proliferativity ratio as calculated in each sample, the cell proliferativity ratio of the cells oriented from the preliminary culture in the tube container was regarded as 100%, and the cell proliferativity ratio of the cells oriented from the preliminary culture in the flask container was calculated as a relative cell proliferativity ratio (relative ratio (%)). The graphs showing the results of the above relative ratio (%) are shown in FIGS. 19 and 20. In FIGS. 19 and 20, the cell proliferativity ratio was not more than 0.8 (Low-growth-rate) and the decrease of the cell viability was considerably observed in the data of the flask container of the samples 10, 14, 15, 16, 20, 22, 24, and 25, and in the data of the tube container of the samples 16 and 24.

Incidentally, FIG. 19 shows a relative ratio (%) as to the samples obtained by seeding and then culturing in a cell number of $1 \times 10^5$ cells, and FIG. 20 shows a relative ratio (%) as to the samples obtained by seeding in a cell number of $1 \times 10^5$ cells. In addition, as to the sample number in the figures, No. 4, 6, 12, 13, and 23 relate to breast cancer cell samples, and the others relate to lung cancer cell samples, in the same way as mentioned above.

(Colorimetric Analysis by a Neutral Red Staining Liquid):

The Neutral Red bio-assay (calorimetric analysis) was carried out in the following procedure.

The culture dish where the collagen gel droplet was prepared was overlaid with the culture medium as obtained by adding a Neutral Red (hereinafter, referred to as NR) staining agent (NR concentration of 25 to 50 μg/ml), and they were stirred and cultured in a 5% $CO_2$ incubator of 37° C. for 2 hours. Thereby, the NR was incorporated in the cells by a living action (phagocytosis) that the cell had. According to this operation, only the live cells can be stained and distinguished. The culture medium containing the NR was washed and removed by a PBS (Phosphate Buffered Saline), and the cells and the NR pigment as incorporated were fixed by a 10% neutral buffered formalin solution. Thereafter, a flat measuring sample was obtained by air-drying.

The above measuring sample was calorimetrically quantified with an image analyzer. Thereby, the integrated image concentration of only the live cancer cells as colored by NR staining was converted to an absorbency value ($OD_{540}$) according to the Lambert-Beer's formula. In addition, the number of the live cancer cells in the globular collagen gel was determined from the resultant absorbency value by converting in the following way.

At first, when the cells were seeded so that the number of the live cells as included per collagen droplet (30 μl) would be 2,500 cells, it was confirmed by a preliminary experiment that the image absorbency value was 20 on average. Accordingly, the above number of the live cells was calculated according to the following converting equation:

Number of live cells (piece/0.5 ml)=[Image absorbency value/20]×2,500 (cell number)×16 (droplet number)

From the value as obtained according to the above converting equation, the yield of the live cells in the various culture supporting base was evaluated.

(Results and Consideration):

In a graph as shown in FIG. 15, from the image absorbency values, observed was the significant difference (t-test=significant level 0.05) such that the tube container is superior because of the difference of the container (difference of the supporting base shape) in 11 samples among 16 samples.

In a graph as shown in FIG. 16, obtained was the result that: in almost all the samples of the tube container, the numbers of the live cells were nearly as large as or greatly larger than the cell number when the seeding was carried out. However, in the case of using the flask container, in many samples, the numbers of the live cells were nearly as large as the cell number when the seeding was carried out, but in not less than half of the samples, the numbers of the live cells were smaller than the cell number when the seeding was carried out. Accordingly, it was observed that the cell collection ratio was lowered. From the above fact, when the tube container is compared with the flask container, it was confirmed that there were many cases where the tube container could achieve enough proliferation to greatly exceed the cell number when the seeding was carried out, and could particularly favorably satisfy the present invention object.

In a graph as shown in FIG. 17, from the image absorbency values, observed was the significant difference (t-test=significant level 0.05) such that the tube container is superior because of the difference of the container (difference of the supporting base shape) in 6 samples among 9 samples.

A graph as shown in FIG. 18 shows results in the case that the cell density was lowered when the seeding was carried out. There were a few cases where, in every supporting base, the numbers of the live cells exceeds the cell number when the seeding was carried out, and there were a few samples in which the numbers of the live cells were nearly as large as the cell number when the seeding was carried out. However, when the tube container is compared with the flask container, it was confirmed that the tube container had a higher cell collection ratio in general and the numbers of the live cells therein were more nearly as large as the cell number when the seeding was carried out.

In graphs as shown in FIGS. 19 and 20, when the preliminary culture is carried out using the tube container, it is found every sample has comparatively high cell proliferativity, and culture tests such as an anticancer agent sensitivity test can sufficiently be carried out and continued.

Incidentally, as to 25 embedded and cultured samples as shown in FIGS. 19 and 20, the samples in which the sufficient cell growth rate (not less than 0.8 time as large as the number of cells as seeded in the embedding culture) could not be obtained was: 8 samples when the flask container was used; and 2 samples when the tube container was used.

From the above test results, it was found that: in the case where the above tube container as shown in FIGS. 13 and 14 was used as a container with the culture supporting base in the culture of the biopsy cancer cells, not only the live cell collection ratio was improved when the preliminary culture was carried out, but also very excellent effects as to maintenance of the cell proliferativity (cell proliferation ability) was displayed in the subsequent culture, in comparison with the case where the above flask container was used. Furthermore, the test success rate can be improved in such as an anticancer agent sensitivity test.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

The invention claimed is:

1. A process for culturing animal cells, which comprises a step of preliminarily culturing animal cells in a culture medium without previously washing the animal cells, wherein in said preliminary culturing step, the animal cells are in a state contaminated with bacteria after having been sampled from a living body,
   wherein said culture medium has a proliferating action and physiological activity-retaining action on the animal cells, and further has a killing action and/or multiplication-inhibition action on bacteria in said preliminary culturing step, said culture medium comprising an antibiotic agent including vancomycin in a concentration of 0.01 to 3 mg/ml to provide the killing action and/or multiplication-inhibition action.

2. A process for culturing animal cells according to claim 1, wherein the antibiotic agent further includes at least two members selected from the group consisting of cell-wall-synthesis inhibitors, protein-synthesis inhibitors, nucleic-acid-synthesis inhibitors, and antifungal agents.

3. A process for culturing animal cells according to claim 1, wherein the sample is obtained by a low-invasive sampling method in which animal cells are sampled from at least one member selected from the group consisting of biopsy cells, materials below thoracoscope or laparoscope, ascites and malignant pleural fluid.

4. A process for culturing animal cells according to claim 1, wherein the culture step is carried out on a surface of a supporting base wherein the supporting base has a layer, including an extracellular matrix, as a cell adhesion factor.

5. A process for culturing animal cells according to claim 4, wherein the extracellular matrix includes at least one member selected from the group consisting of collagen, fibronectin, laminin, vitronectin, cadherin, gelatin, peptides, and integrin.

6. A process for culturing animal cells according to claim 4, wherein the supporting base has a surface area of 0.01 to 25.0 $cm^2$.

7. A process for culturing animal cells, which comprises a second culturing step subsequent to said preliminary culturing step of claim 1, wherein said second culturing step includes:
   seeding cells by dispersing the animal cells obtained from the preliminary culture step, into a collagen solution;
   placing a droplet or droplets of the collagen solution on a surface of a supporting base material and allowing the droplet or droplets to gel to form and fix on the surface of the supporting base material to form a globular collagen gel having a convex surface; and
   contacting the collagen gel with a liquid culture medium and further culturing the animal cells in a proliferative culturing step.

* * * * *

UNITED STATES PATENT AND TRADEMARK OFFICE
CERTIFICATE OF CORRECTION

PATENT NO. : 7,247,481 B2
APPLICATION NO. : 10/122220
DATED : July 24, 2007
INVENTOR(S) : Kazuhiko Minamigawa et al.

It is certified that error appears in the above-identified patent and that said Letters Patent is hereby corrected as shown below:

On The Title Page
Item
(30) Foreign Application Priority Data

Apr. 23, 2001   JAPAN................2001-124814
Jan. 23, 2002   JAPAN................2002-014724

Signed and Sealed this

Twenty-third Day of October, 2007

JON W. DUDAS
*Director of the United States Patent and Trademark Office*